(12) United States Patent
Klein et al.

(10) Patent No.: US 11,975,445 B2
(45) Date of Patent: May 7, 2024

(54) SYSTEM FOR CONNECTING END EFFECTORS TO ROBOT ARMS THAT OPERATE UNDER STERILE CONDITIONS

(71) Applicants: DePuy Synthes Products, Inc., Raynham, MA (US); Rheinisch-Westfälische Technische Hochschule (RWTH) Aachen, Aachen (DE)

(72) Inventors: Matias de la Fuente Klein, Aachen (DE); Lukas Theisgen, Aachen (DE); Manuel Vossel, Aachen (DE); Klaus Radermacher, Aachen (DE); Gerd Petasch, Aachen (DE)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 251 days.

(21) Appl. No.: 17/396,189

(22) Filed: Aug. 6, 2021

(65) Prior Publication Data
US 2023/0045591 A1   Feb. 9, 2023

(51) Int. Cl.
*B25J 19/00*  (2006.01)
*A61B 17/00*  (2006.01)
(Continued)

(52) U.S. Cl.
CPC ........... *B25J 19/0075* (2013.01); *A61B 34/30* (2016.02); *A61B 34/70* (2016.02); *A61B 46/10* (2016.02);
(Continued)

(58) Field of Classification Search
CPC ... B25J 19/0075; B25J 15/0408; A61B 34/30; A61B 2017/00477
See application file for complete search history.

(56) References Cited

U.S. PATENT DOCUMENTS

| | | | |
|---|---|---|---|
| 5,524,180 A | 6/1996 | Wang et al. | |
| 5,591,119 A * | 1/1997 | Adair | A61B 46/10 600/122 |

(Continued)

FOREIGN PATENT DOCUMENTS

| | | |
|---|---|---|
| CN | 107249496 A | 10/2017 |
| EP | 2211748 B1 | 4/2018 |

(Continued)

OTHER PUBLICATIONS

International Search Report and Written Opinion for PCT/IB2022/056594 dated Nov. 7, 2022.

*Primary Examiner* — Jake Cook
(74) *Attorney, Agent, or Firm* — Kramer & Amado, P.C.

(57) ABSTRACT

An end effector is removably connected to a robot arm under sterile conditions with an arm mount module configured to be connected to the robot arm, and an arm drape module configured to be removably connected to the arm mount module by a first locking mechanism. A third module may be configured to be removably connected to the arm drape module by a second locking mechanism. A sterile hand drape module may be configured to be removably connected to the arm drape module by the second locking mechanism; and a hand mount module may be configured to be removably connected to the hand drape module by a third locking mechanism, and to be connected to the end effector or the hand mount module is the end effector itself. A transmission pathway for signals, electrical energy, or mechanical energy is provided between the robot arm and the end effector.

23 Claims, 23 Drawing Sheets

(51) Int. Cl.
    *A61B 34/00*     (2016.01)
    *A61B 34/30*     (2016.01)
    *A61B 46/10*     (2016.01)
    *B25J 15/04*     (2006.01)

(52) U.S. Cl.
    CPC . *B25J 15/0408* (2013.01); *A61B 2017/00477* (2013.01); *A61B 2034/305* (2016.02)

(56) References Cited

U.S. PATENT DOCUMENTS

| | | | |
|---|---|---|---|
| 6,132,368 | A | 10/2000 | Cooper |
| 7,699,855 | B2 | 4/2010 | Anderson et al. |
| 7,727,244 | B2 | 6/2010 | Orban, III et al. |
| 7,947,050 | B2 | 5/2011 | Lee et al. |
| 7,963,913 | B2 | 6/2011 | Devengenzo et al. |
| 8,220,468 | B2 | 7/2012 | Cooper et al. |
| 8,720,448 | B2 | 5/2014 | Reis et al. |
| 8,740,881 | B2 | 6/2014 | Ortmaier et al. |
| 8,910,637 | B2 | 12/2014 | Winer |
| 8,998,930 | B2 | 4/2015 | Orban, III |
| 9,603,671 | B2 | 3/2017 | Hladio et al. |
| 9,629,680 | B2 | 4/2017 | Winer |
| 9,713,506 | B2 | 7/2017 | Fanson et al. |
| 9,724,163 | B2 | 8/2017 | Orban |
| 10,034,715 | B2 | 7/2018 | Fanson et al. |
| 10,039,605 | B2 | 8/2018 | Kostrzewski et al. |
| 10,357,324 | B2 | 7/2019 | Flatt et al. |
| 2005/0094269 | A1 | 5/2005 | Moses et al. |
| 2014/0007732 | A1 | 6/2014 | Ogawa |
| 2015/0202009 | A1 | 7/2015 | Nussbaumer et al. |
| 2016/0354582 | A1 | 12/2016 | Yu et al. |
| 2017/0000320 | A1 | 1/2017 | Wilson |
| 2018/0125597 | A1 | 5/2018 | Gogarty et al. |
| 2018/0168752 | A1 | 6/2018 | Scheib et al. |
| 2018/0168761 | A1 | 6/2018 | Vargas et al. |
| 2018/0168762 | A1 | 6/2018 | Scheib et al. |
| 2018/0168763 | A1 | 6/2018 | Schelb et al. |
| 2018/0200021 | A1 | 7/2018 | Scheib et al. |
| 2018/0206931 | A1 | 7/2018 | Scheib et al. |
| 2019/0000567 | A1 | 1/2019 | Allen et al. |
| 2019/0000580 | A1 | 1/2019 | Scheib et al. |
| 2019/0099232 | A1 | 4/2019 | Soto et al. |
| 2020/0061847 | A1 | 2/2020 | Dixon |
| 2020/0170724 | A1* | 6/2020 | Flatt .................... A61B 34/70 |
| 2020/0330173 | A1 | 10/2020 | Kapadia |
| 2021/0197401 | A1 | 7/2021 | Weintraub |

FOREIGN PATENT DOCUMENTS

| | | |
|---|---|---|
| EP | 3609422 A1 | 2/2020 |
| KR | 101105280 B1 | 1/2012 |
| WO | 2015188071 A2 | 12/2015 |
| WO | 2016065458 A1 | 5/2016 |
| WO | 2018111575 A1 | 6/2018 |
| WO | 2019036004 A1 | 2/2019 |

* cited by examiner

SYSTEM FOR CONNECTING END EFFECTORS TO ROBOT ARMS THAT OPERATE UNDER STERILE CONDITIONS

TECHNICAL FIELD

Various exemplary embodiments disclosed herein relate generally to systems for connecting end effectors, e.g., tools, to robot arms for manipulation of the same.

BACKGROUND

Robot-assisted surgery allows doctors to perform complex procedures with increased precision, compared to conventional techniques. Robot-assisted surgery allows minimally invasive surgery to be performed through tiny incisions. However, robot arms suitable for medical uses are expensive. Some robot arms are designed for particular tasks, or require particular end effectors or tools.

A robot arm for use in an industrial or medical setting typically includes from 1 to 7 or more degrees of freedom. Such degrees of freedom include degrees of rotational or translational motion. The base and the end effector are connected by a series of rigid bodies with intervening joints, e.g., revolute joints, prismatic joints, helical joints, or spherical joints; these joints introduce degrees of freedom to the system.

In an exemplary robot arm, an end effector may be connected to a robot arm having a series of revolute joints, with each revolute joint introducing a single degree of freedom. In such a robot arm, multiple rigid bodies may be connected to a base by a series of revolute joints allowing rotation of the first rigid body about an axis. An end effector may be connected to a rigid body by a further revolute joint.

In some robot arms, one or more revolute joints may be replaced by a prismatic joint or a helical joint, allowing extension or retraction of one rigid body relative to another rigid body.

In an exemplary robot arm, sufficient joints are introduced to provide the robot arm with six or seven degrees of freedom. With six degrees of freedom, an end effector may be positioned at any desired position within a defined space, at any desired angle. With fewer than six degrees of freedom, the end effector may be positioned at certain desired positions within the defined space, at certain desired angles. With more than 6 degrees of freedom, an end effector may be positioned at any desired position within a defined space, at any desired angle, allowing a given joint of the robot to be moved without changing this position and orientation.

In a setting where multiple procedures may need to be carried out with robot arms, it is undesirable for a hospital or other medical institution to be forced to purchase multiple robot arms, where each robot arm performs a specific task. Similarly, in an industrial setting, it is undesirable to replace an entire robot arm when an end effector needs to be modified or replaced. Rather, it is desirable to use interchangeable end effectors on a single robot arm. In many cases, it is desirable to quickly replace or exchange end effectors while maintaining sterility in a surrounding environment.

SUMMARY

In light of the present need for systems for interchangeably connecting end effectors to robot arms, a brief summary of various embodiments is presented. Some simplifications and omissions may be made in the following summary, which is intended to highlight and introduce some aspects of the various embodiments, but not to limit the scope of the invention. Detailed descriptions of various embodiments adequate to allow those of ordinary skill in the art to make and use the inventive concepts disclosed herein will follow in later sections.

[Summary to be filled in later]

BRIEF DESCRIPTION OF THE DRAWINGS

In order to better understand various exemplary embodiments, reference is made to the accompanying drawings, wherein.

DETAILED DESCRIPTION

Figure 1:
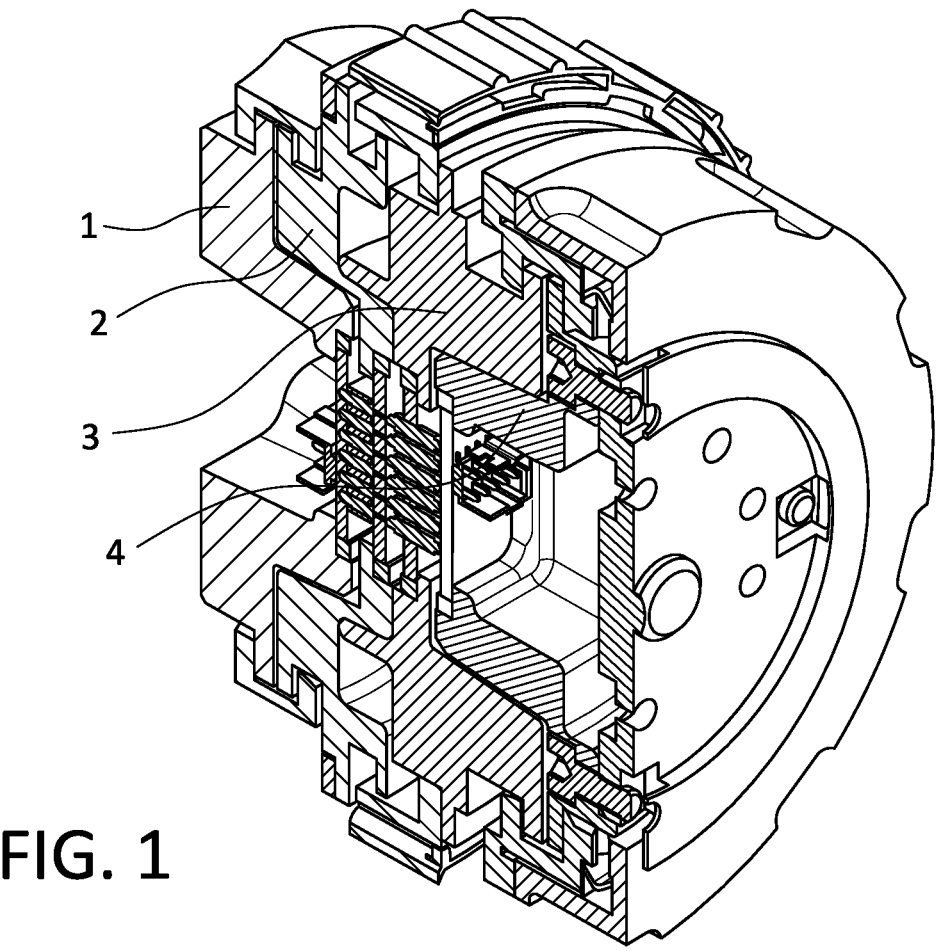
FIG. 1 shows a system for connecting a robot arm to a non-sterile end effector.

According to the foregoing, various exemplary embodiments provide for connection of a variety of tools, including medical or industrial tools, to a single robot arm by a standardized set of interface modules.

In the present disclosure, the term "robot arm" encompasses any type of mechanical or kinematic arm which is jointed to allow linear motion, rotary motion, or a combination thereof. The mechanical arm may be an automated arm operating under human control, or an automated arm controlled by a computer or an artificial intelligence. The mechanical arm may be a passive arm directly manipulated by a human operator.

In the present disclosure, the term "flush" may mean that two items are coplanar. However, two parallel surfaces may also be considered "flush" even if a first surface is slightly recessed or elevated, relative to a second surface, e.g., recessed or elevated relative to the first surface by 10 microns to 1,000 microns. Thus, for the purposes of this disclosure, a first surface and a second surface are considered flush if:

The surfaces are coplanar; or

The second surface is recessed or elevated by up to 1,000 microns, relative to the first surface.

Referring now to the drawings, in which like numerals refer to like components or steps, there are disclosed broad aspects of various exemplary embodiments.

The present disclosure relates to a system for connecting an end effector, also referred to as a "hand," to a robot arm. Thus, a "hand mount module," is understood to be a module for mounting to an end effector. An end effector is a peripheral device that attaches to a robot arm, allowing the robot arm to perform a desired task. Most end effectors are mechanical or electromechanical, and serve as grippers, process tools, or sensors. In a medical setting, end effectors may include tools such as drills, saws, and other cutting implements. End effectors may also include additional mechanisms, such as actuated linkages. End effectors may also include endoscopes or other sensor devices. A variety of tools and sensors may be used as end effectors in an industrial setting.

In the present disclosure, an "arm mount module" is a module which is permanently or temporarily connected to a robot arm. In some embodiments, the arm mount module may be an integral part of a robot arm.

In the present disclosure, a "hand mount module" and an "end effector module" are synonymous terms used to describe a module which is permanently or temporarily connected to a manipulative tool or a sensor, i.e., an end effector. In some embodiments, the hand mount module or end effector module may be an integral part of a desired end effector. In other embodiments, the hand mount module or end effector module is removably attached to a desired end effector.

In the present disclosure, an "arm drape module" and "a hand drape module" may be releasably connected together, and may be used together to connect a hand mount module to an arm mount module, thereby connecting an end effector to a robot arm. The arm drape module may include a sterile drape which covers the arm mount module and the robot arm connected thereto. The hand drape module may include a sterile drape which covers the end effector module, and may cover an end effector connected thereto.

Figure 2A:
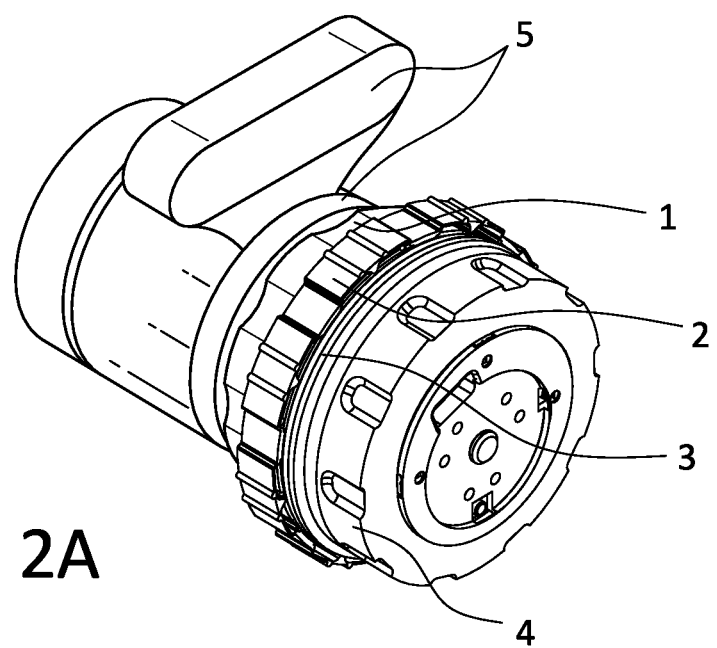
FIG. 2A shows a system of FIG. 1 connected to a robot arm.
Figure 2B:
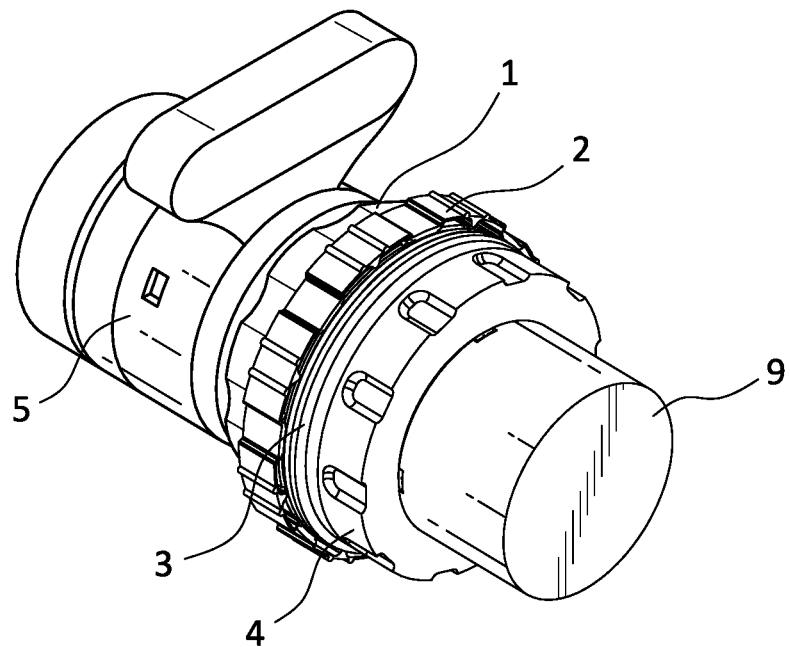
FIG. 2B shows a system of FIG. 1 connected to a robot arm and an end effector.

FIG. 1 shows a system for connecting a robot arm to an end effector. The system includes an arm mount module 1 for connection to a robot arm, and an hand mount module 4 for connection to an end effector. The hand mount module 4 could also be the end effector itself. An arm drape module 2 removably connects to the arm mount module 1, and a hand drape module 3 removably connects to both arm drape module 2 and hand mount module 4. As seen in FIG. 2A, arm mount module 1 is connected to an end 5 of a robot arm. Arm mount module 1 may be bolted or screwed to the robot arm. As seen in FIG. 2B, hand mount module 4 is connected to an end effector 9, and arm mount module 1 is connected to a robot arm 5. In some embodiments, hand mount module 4 is permanently connected to an end effector 9, and removably connected to hand drape module 3. Arm mount module 1 may be permanently connected to robot arm 5, and removably connected to arm drape module 2.

Figure 4:
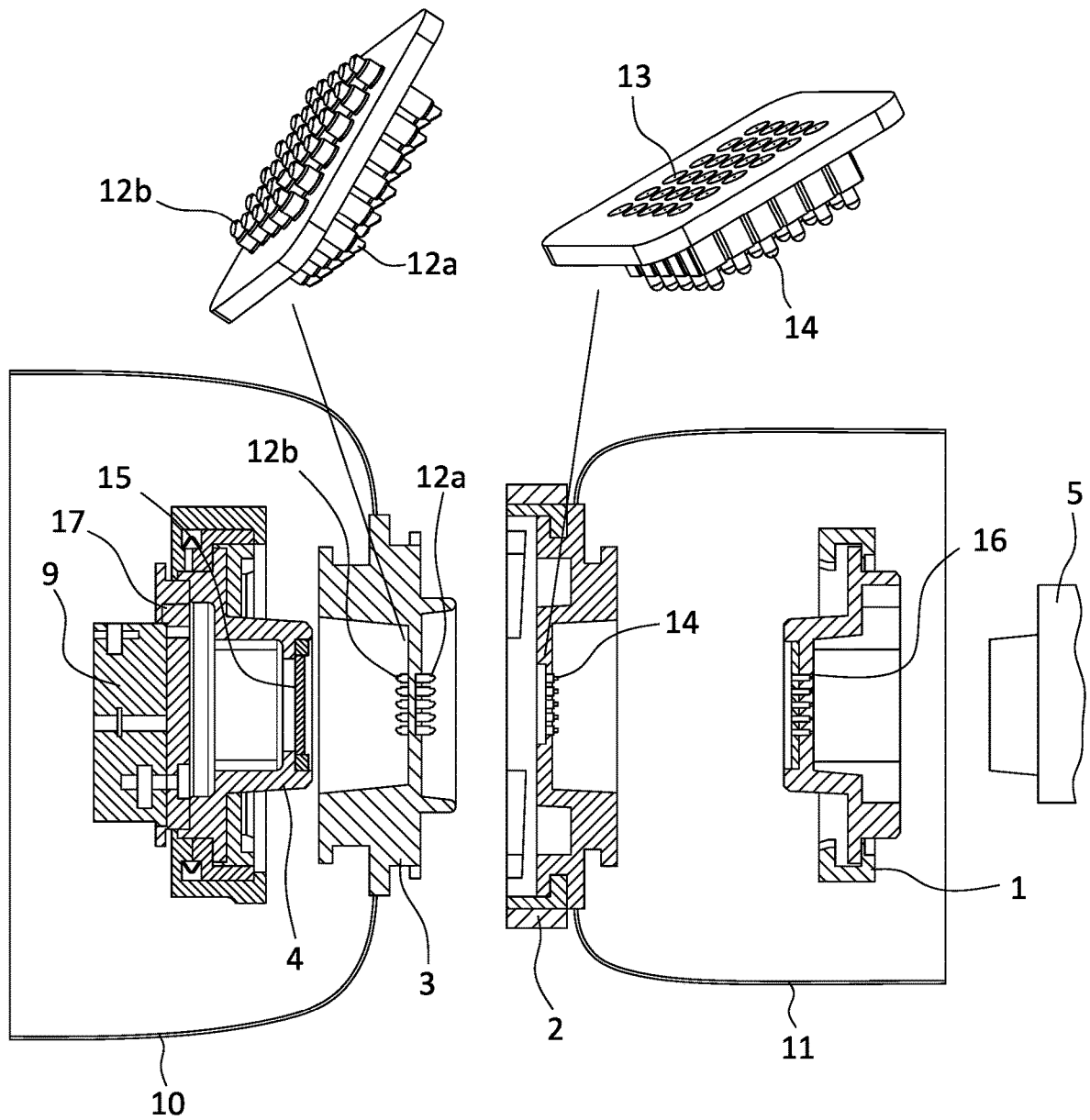
FIG. 4 shows an exploded view of the assembly of FIG. 2.

In the system of FIGS. 1 and 4, a modular coupling mechanism allows connection between a carrier structure and an end effector or hand. The system of FIG. 1 includes 4 modules, including:

a reusable arm mount module 1, which may be permanently mounted on an unsterile carrier structure, e.g., a robot arm 5;

a disposable arm drape module 2 which is temporarily mounted on the arm mount module 1;

a disposable hand drape module 3 which is temporarily mounted on the arm drape module 2; and a reusable but unsterile hand mount module 4.

As shown in FIG. 4, hand mount module 4 is permanently mounted on an unsterile end effector 9 that can be robotic or active in general. End effector 9, as shown in FIGS. 2B and 4, is a generic end effector; in practice, a variety of end effectors including saws, drills, and sensors or mechanisms may be used as end effectors 9. The arm drape module 2 and hand drape module 3 may be provided as sterile or sterilizable components, for use in a single procedure in sterile industrial settings or medical settings; modules 2 and 3 may be discarded after a single use. Arm drape module 2 may include a sterile drape 11 for covering arm mount module 1 and robot arm 5. Hand drape module 3 may include a sterile drape 10 for covering hand mount module 4 and end effector 9. Embodiments using a sterile drape to cover a non-sterile robot arm, a non-sterile end effector, or both, may be used in medical settings, i.e., during surgery, or in industrial settings requiring sterile conditions, i.e., settings used for manufacture of electronic devices.

In some embodiments, the end of a robot arm may include a planar surface which may be mounted to the arm mount module 1. The planar surface may be mounted to the arm mount module temporarily or permanently. Robot arm 5 may also include a socket which allows electrical signals to pass to and from the robot arm to the arm mount module 1.

Figure 3:
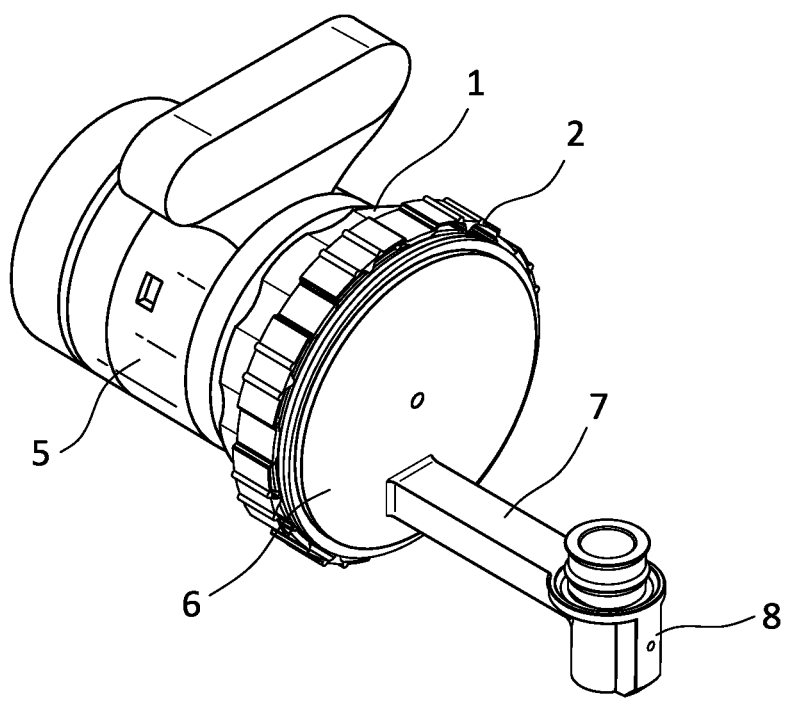
FIG. 3 shows a system for connecting a robot arm to a sterile end effector.

As seen in FIG. 3, the hand drape module 3 and the hand mount module 4 may be replaced with a reusable or disposable end effector module 6 for holding a tool. In the embodiment of FIG. 3, reusable or disposable end effector module 6 includes an arm 7 and a mount 8 for connecting tools to end effector module 6. The mount 8 may include a tubular element for receiving a drill or other tools.

FIG. 3 shows a system for removably connecting an end effector to a robot arm, including:

an arm mount module 1 having a front surface and a rear surface, which may be connected to a robot arm 5;

an arm drape module 2 having a front surface and a rear surface, which may be removably connected to the front surface of the arm mount module 1 by a first locking mechanism; and an end effector module 6 configured to be removably connected to the arm drape module 2 by a second locking mechanism. The end effector module 6 may be removably connected to a separate end effector, or the end effector module 6 may itself function as an end effector.

In FIG. 3, the end effector module 6 includes a base configured to be removably connected to the arm drape module 2, and an arm 7 having a mount 8 configured to removably receive a tool. In various embodiments, the arm drape module 2 and the end effector module 6 are sterile or made of sterilizable materials. The arm drape module 2 may include a drape made of a sterile fabric or plastic material, which is configured to cover the arm mount module and the robot arm.

In the system of FIG. 3, a modular coupling mechanism allows connection between a carrier structure and a disposable end effector. The system of FIG. 3 includes 3 modules, including:

a reusable arm mount module 1, which is permanently mounted on an unsterile carrier structure, e.g., a robot arm 5;

a disposable arm drape module 2 which is temporarily mounted on the arm mount module 1; and a disposable end effector module 6 which is temporarily mounted on the arm drape module 2 which may include a rigid guide sleeve 8 for positioning a saw or drill.

Arm drape module 2 and disposable end effector module 6 may be sterile or sterilizable, for use in sterile industrial settings or medical settings. Arm drape module 2 may include a sterile drape for covering arm mount module 1 and robot arm 5. FIG. 4 shows an exploded view of the system of FIG. 1 for use with a robot arm 5 and an end effector 9 in a medical setting. In such settings, arm mount module 1 and hand mount module 4 may not be sterile. In some embodiments, hand mount module 4 may function as an end effector; in others, an end effector may be secured to module 4. However, arm drape module 2 and hand drape module 3 may be provided in a sterile condition, and used to provide a sterile connection between modules 1 and 4. Arm drape module 2 and hand drape module 3 may be disposable modules provided in sterile packaging, or either or both of modules 2 and 3 may be reused after sterilization in an autoclave or similar apparatus. Modules 2 and 3 may be provided with sterile plastic or fabric drapes to cover the robot arm and the end effector, preventing infectious agents, e.g., microorganisms, from entering a surgical site. As seen in FIG. 4, non-sterile arm mount module 1 is connected, e.g., with bolts or screws, to a robot arm 5, where an indentation on a rear surface of module 1 engages a projection on robot arm 5. Arm drape module 2 is then removably connected to arm mount module 1. Arm drape module 2 is sterile, and may be provided with a sterile drape 11 which may be used to cover the non-sterile arm mount module 1 and non-sterile robot arm 5. Drape 11 prevents infectious agents from the non-sterile parts 1 and 5 from contaminating the surgical site. As seen in FIG. 4, arm mount module 1 has electrical contacts 16 configured to receive electrical signals from robot arm 5. The contacts may be provided on a printed circuit board. The contacts can be designed and mounted on the printed circuit board so that no particles or liquids can pass between modules through the circuit board, allowing the circuit board to function as a sterile barrier between adjacent modules. Arm drape module 2 has electrical connectors with:

rear contacts 14 on a rear surface of module 2, which are configured to engage contacts 16 when module 2 is mounted on module 1; and front contacts 13 on a front surface of module 2.

In various embodiments, FIG. 4 shows a system for removably connecting an end effector to a robot arm, including:

an arm mount module 1 having a front surface and a rear surface, where the rear surface of the arm mount module 1 is configured to be connected to a robot arm 5;

an arm drape module 2 having a front surface and a rear surface, where the rear surface of the arm drape module 2 is configured to be removably connected to the front surface of the arm mount module 1 by a first locking mechanism;

a hand drape module 3 having a front surface and a rear surface, where the rear surface of the hand drape module 3 is configured to be removably connected to the front surface of the arm drape module 2 by a second locking mechanism; and a hand mount module 4 having a front surface and a rear surface, where:

the rear surface of the hand mount module 4 is configured to be removably connected to the front surface of the hand drape module 3 by a third locking mechanism, and the front surface of the hand mount module 4 is configured to be connected to the end effector 9. The first locking mechanism, the second locking mechanism, and the third locking mechanism may be the same or different.

Also as seen in FIG. 4, a front plate 17 on non-sterile hand mount module 4 is configured to be connected, e.g., with bolts or screws, to a non-sterile end effector 9. Hand drape module 3 is then removably connected to hand mount module 4. Hand drape module 3 is sterile, and may be provided with a sterile drape 10 which may be used to cover the non-sterile end effector and hand mount module 4. Drape 10 prevents infectious agents from the non-sterile module 4 and end effector from contaminating the surgical site. As seen in FIG. 4, hand mount module 4 has electrical contacts 15, which are configured to transmit electrical signals to the end effector. As discussed above, the contacts may be provided on a printed circuit board which functions as a sterile barrier between adjacent modules. Hand drape module 3 has retractable or spring-mounted electrical connectors 12. A front surface of each connector 12 includes a contact 12*b*, which is configured to engage a contact 15 when module 3 is mounted on module 4. A rear surface of each connector 12 includes a contact 12*a*. When hand drape module 3 is mounted on arm drape module 2, electrical contacts 12*a* on hand drape module 3 are configured to engage electrical contacts 13 on the front surface of arm drape module 2, establishing an electrical pathway from robot arm 5 to the end effector 9. Hand mount module 4 is configured to be connected to an end effector 9, also referred to herein as hand 9. The system disclosed herein is a modular coupling mechanism between a carrier structure, e.g., robot arm 5, and an end effector 9, or hand 9, for the transmission of electrical energy and/or electrical signals between the robot arm and the end effector. Since multiple contacts are present in each module, a single signal may be passed between adjacent modules using multiple contacts for redundancy. If a single contact fails to transmit a signal, other contacts may transmit the signal.

In various embodiments, mechanical, hydraulic, or pneumatic energy may be transmitted between modules instead of, or in addition to, electrical energy. A sterile adapter for use in a robotic surgical system may include a first module comprising a plurality of tool engagement features, wherein each tool engagement feature is mateable with a corresponding adapter engagement feature on an adjacent second module or an end effector. At least one rotatable coupler supported by the first module may be configured to communicate torque from an output drive of the first module to an input drive of the second module or the end effector. Such a system is shown in US 2018/0168752, incorporated herein by reference.

As will be discussed in further detail below, various embodiments disclosed herein relate to a modular coupling mechanism between a carrier structure, e.g., a robot arm 5, and end-effectors (hands) 9. The modular coupling mechanism is fail-safe through use of various locking mechanisms. These locking mechanisms include:

self-locking mechanisms with acoustic or tactile feedback through snap-in pins;

radial safety-locks, where a loose outer ring with projections or teeth thereon is radially compressed onto an inner ring to enable locking; and/or axial safety-locks, where teeth on axially spaced rings must engage to enable locking.

The system is easy for a user to operate in a medical or industrial setting, as simple rotary movements of the various modules allow the quick exchange of multiple disposable and/or reusable end-effectors or hands without breaking the sterile barrier. In various embodiments, the systems disclosed herein allow rapid exchange of one end effector for another end effector in a sterile or non-sterile environment. A first hand mount module 4 carrying a first end effector 9 can be disengaged from hand drape module 3, and replaced with a second hand mount module 4 carrying a second end effector 9.

Figure 5:
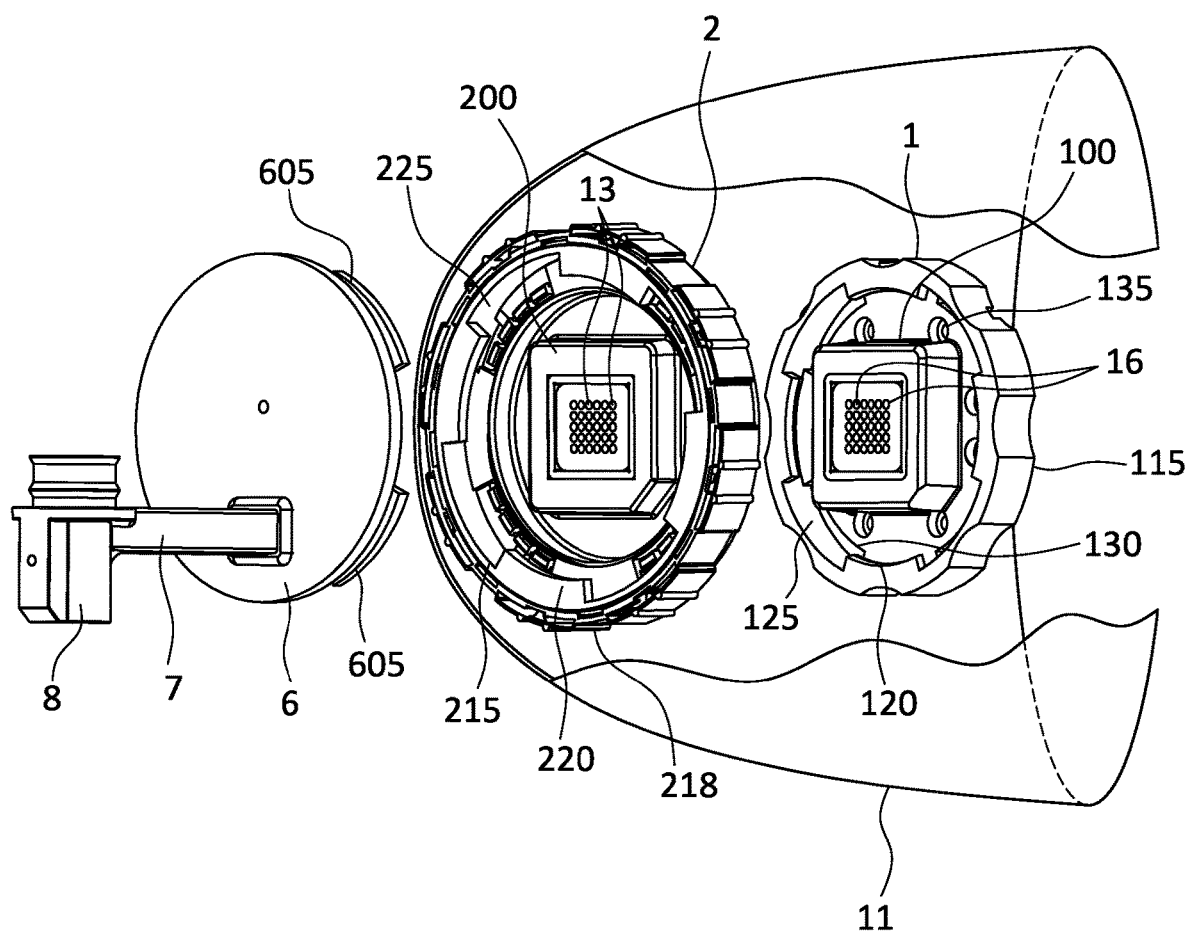
FIG. 5 shows an exploded view of the assembly of FIG. 3.

FIG. 5 shows an exploded view of the assembly of FIG. 3. The system of FIG. 5 includes an arm mount module 1 for connection to a robot arm, and a reusable or disposable end effector module 6 for holding a tool. In the embodiment of FIG. 5, reusable or disposable end effector module 6 includes an arm 7 and a mount 8 for connecting tools to end effector module 6. Arm drape module 2 is removably connected to both arm mount module 1 and to end effector module 6. Arm drape module 2 is sterile, and may be provided with a sterile drape 11 which may be used to cover the non-sterile arm mount module 1 and non-sterile robot arm 5. Sterile drape 11 may be part of module 2, and have a sealed connection to module 2 which prevents transmission of contaminants around or through drape 11. Reusable or disposable end effector module 6 may be provided as a sterile component, or may be sterilized in an autoclave between uses. Consequently, end effector module 6 does not require a sterile drape. Arm mount module 1 and arm drape module 2 will be described in more detail below.

Although the above discussion focuses on manipulation of medical implements by a robot arm in a sterile environment, the systems described herein may be used for connecting tools to robot arms for manipulation or construction of machinery in an industrial setting. The systems described herein may be used for manufacturing electronic equipment in an industrial setting under sterile conditions.

FIGS. 6 to 9 show arm mount module 1, where a rear surface of arm mount module 1 (shown in FIG. 9) is configured to be connected to a robot arm.

Figure 6:
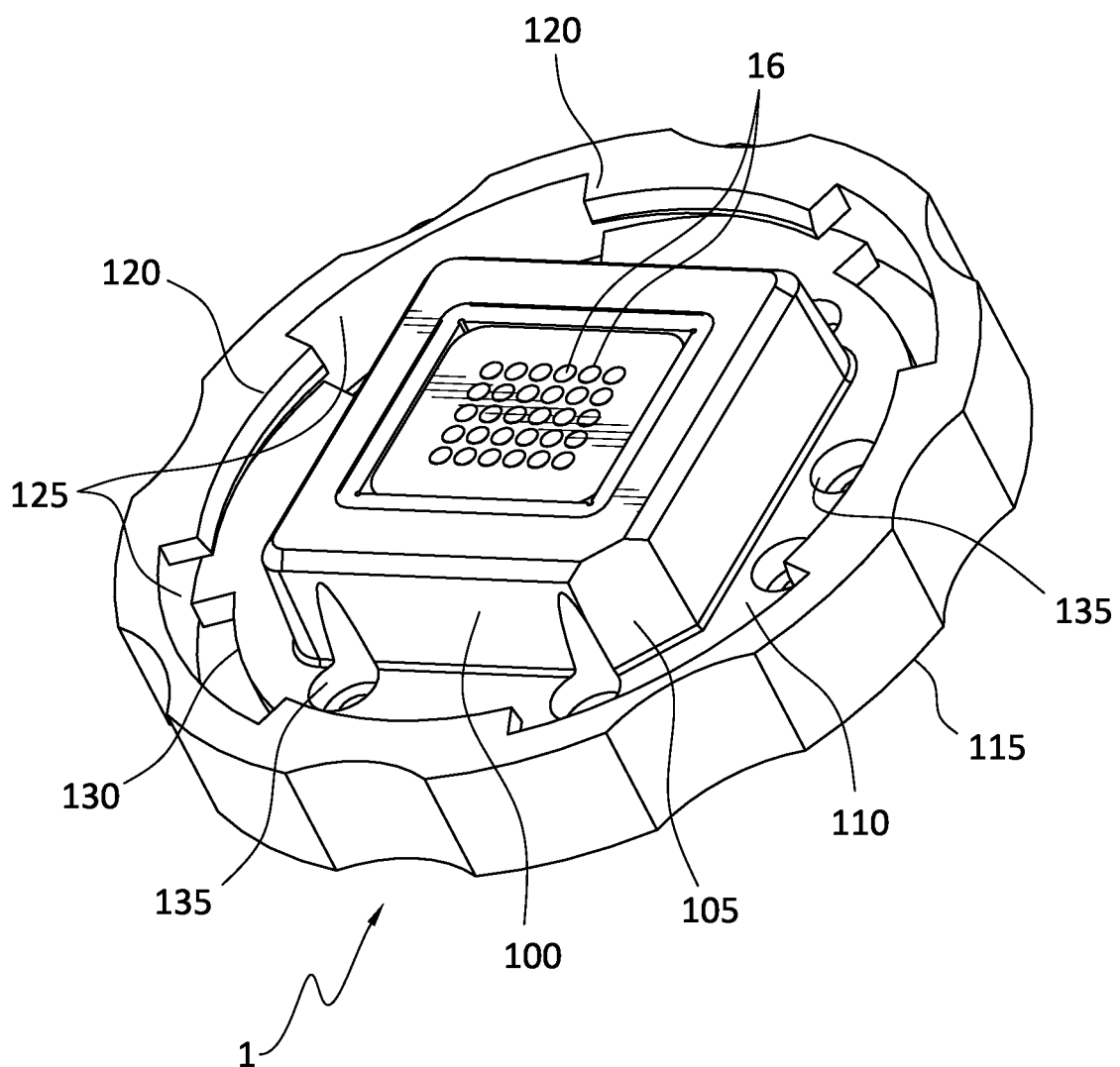
FIGS. 6 to 9 show the arm mount module, as used in the assembly of FIGS. 2 and 3.
Figure 7:
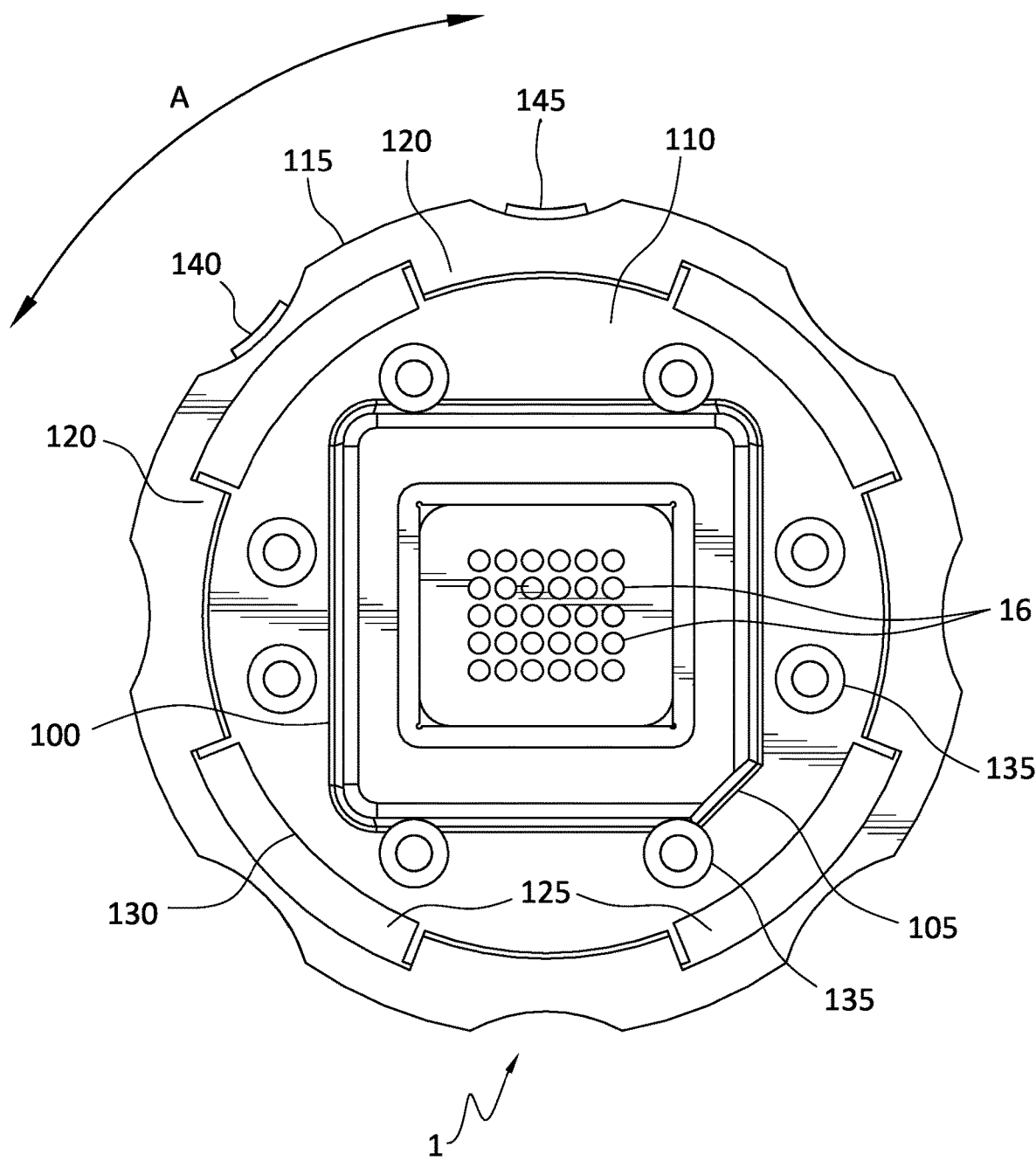

FIGS. 6 and 7 show a perspective view and a front plan view of a front surface of an arm mount module 1, respectively. The front surface of the arm mount module 1 is configured to be connected to arm drape module 2, shown in FIG. 10. As seen in FIG. 6, arm mount module 1 includes an elevated rectangular region 100, with electrical contacts 16 thereon. Contacts 16 may be flush with an upper surface of elevated region 100, allowing easy cleaning, disinfection, and/or sterilization prior to use. Contacts 16 may also be slightly recessed or elevated, relative to the upper surface of elevated region 100, e.g., recessed or elevated relative to the surrounding surface by 10 microns to 1,000 microns. Elevated region 100 may have inclined surfaces, and may, for example, be a truncated cone or a truncated pyramid of 3 or more sides. In some embodiments, elevated region 100 is a regular or irregular polygon. A planar surface 105 may replace at least one corner of region 100, to facilitate and enforce the correct orientation of the connection between arm mount module 1 and arm drape module 2. Elevated region 100 is surrounded by a planar region 110, which contains holes 135 therethrough, where the holes 135 receive screws or bolts for connecting arm mount module 1 to a robot arm 5. Planar region 110 contains a plurality of arcuate spaces 130 in its periphery.

A rotatable ring 115 is mounted on arm mount module 1, and is configured to rotate reversibly from a first position to a second position. Rotatable ring 115 has a plurality of tabs 120, with spaces 125 between each pair of adjacent tabs. Tabs 120 on ring 115 serve as a first locking feature. Referring to FIGS. 6 and 7, ring 115 on arm mount module 1 is reversibly rotatable in the direction of arrow A, between a locked position and an unlocked position. In the unlocked position, spaces 125 in ring 115 are configured to receive tabs 230 on a rear surface of arm drape module 2 (tabs 230, which serve as a second locking feature, are visible in FIGS. 12, 13 and 17, which will be discussed later). In the locked position, tabs 120 in ring 115 are configured to be rotated in front of tabs 230 on arm drape module 2, locking arm drape module 2 to arm mount module 1. Markers 140 and 145 may be used to signal whether ring 115 on arm mount module 1 is in an unlocked position or a locked position.

Figure 8:
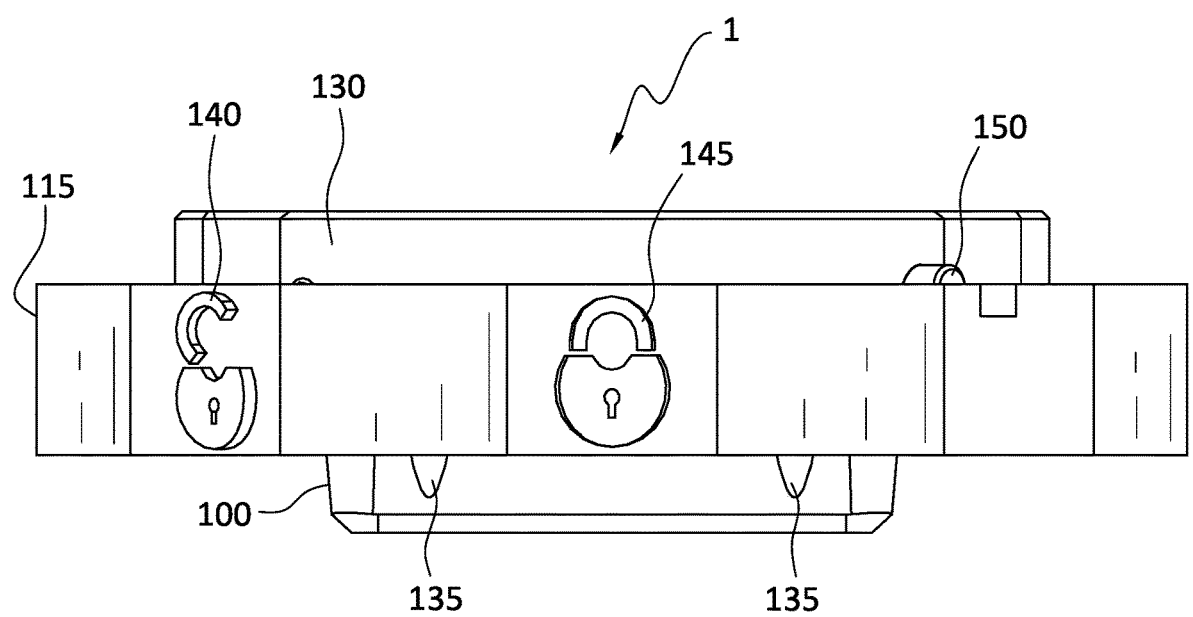

FIG. 8 shows a side view of an arm mount module 1, and provides better views of marker 140, indicating that arm mount module 1 is in an unlocked position, and marker 145, indicating that arm mount module 1 is in a locked position. FIG. 8 additionally shows arcuate spaces 130 in the periphery of planar region 110, and pins 150 mounted in spaces 130. Pins 150 serve as a feature which controls the extent of rotation of ring 115 in the direction of arrow A, as described below.

Figure 9:
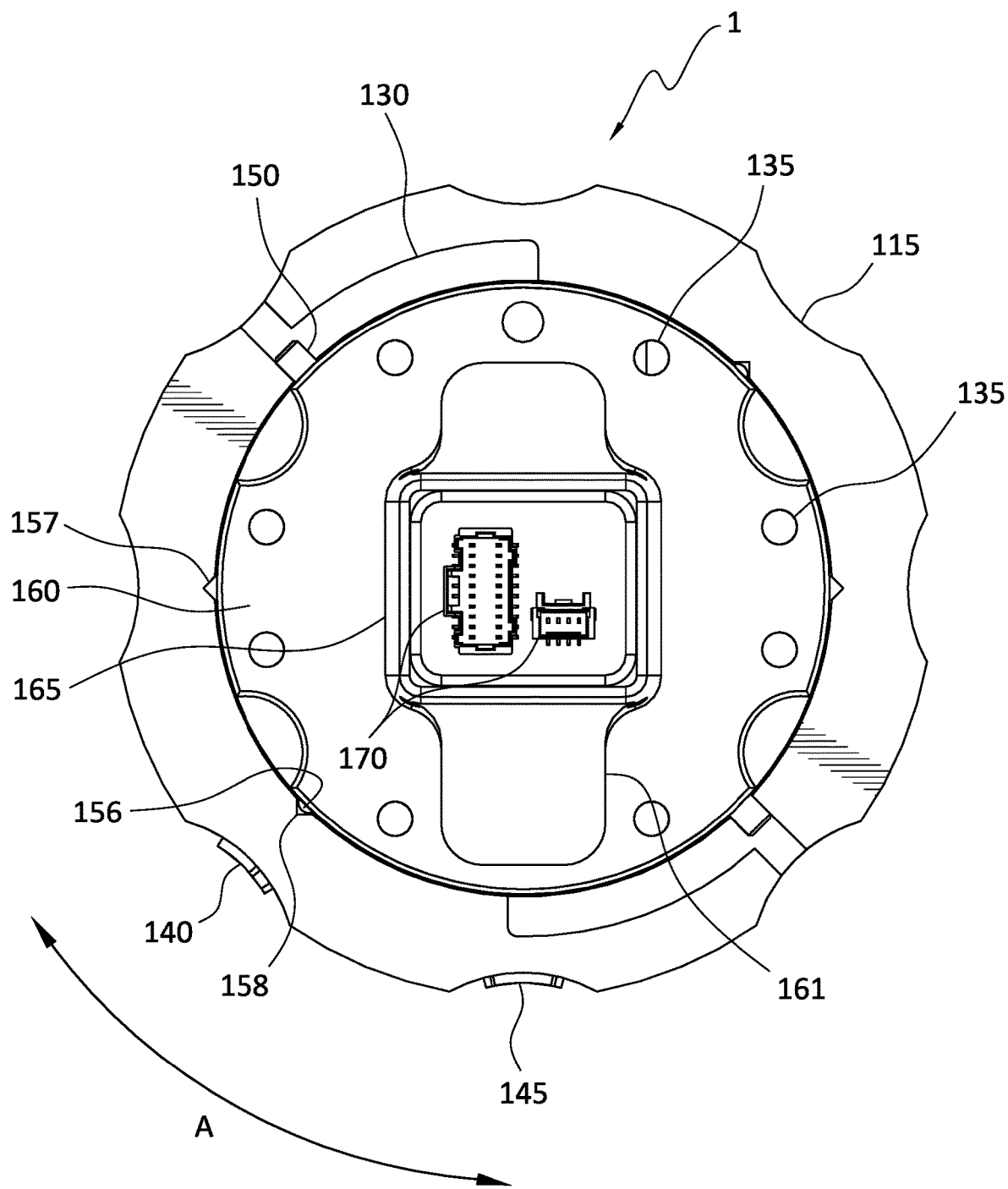

FIG. 9 shows a rear view of an arm mount module 1. The rear of arm mount module 1 includes a planar surface 160, with exit openings for the holes 135 for bolting module 1 to the robot arm. A depression 161 is configured to fit over a corresponding projection on a robot arm 5. An indentation 165 in depression 161 is positioned to correspond to elevated region 100 on front surface 110, and includes ports or sockets 170 for receiving electrical connectors from robot arm 5. As discussed before, rotatable ring 115 is mounted on arm mount module 1, and is configured to rotate reversibly from an unlocked position to a locked position in the direction of arrow A. When rotatable ring 115 is in an unlocked position, retractable pins or bearings 156 are pressed into a notch 158. When rotatable ring 115 enters a locked position, retractable pins or bearings 156 move radially outward into notches 157, locking ring 115 in position. As discussed above, in the locked position, tabs 120 in the front of ring 115 are configured to be rotated in front of tabs 235 on arm drape module 2 to lock arm drape module 2 to arm mount module 1. As pins or bearings 156 move radially into notches 158, tactile or audible feedback may be provided to indicate that the ring 115 is in a locked position. When ring 115 is rotated in the direction of arrow with sufficient force, retractable pins or bearings 156 may exit notches 158, and enter notches 157. This allows ring 115 to be rotated into an unlocked position so that an arm mount module 1 may be separated from an arm drape module 2. As ring 115 rotates in the direction of arrow A, arcuate notches 130 move relative to fixed pins 150. Pins 150 and notches 130 serve to prevent ring 115 from rotating in the direction of arrow A in a first direction beyond a locked position, or in a second direction beyond an unlocked position.

FIGS. 10 to 13 show arm drape module 2, where a rear surface of arm drape module 2 (shown in FIG. 13) is configured to be connected to arm mount module 1.

Figure 10:
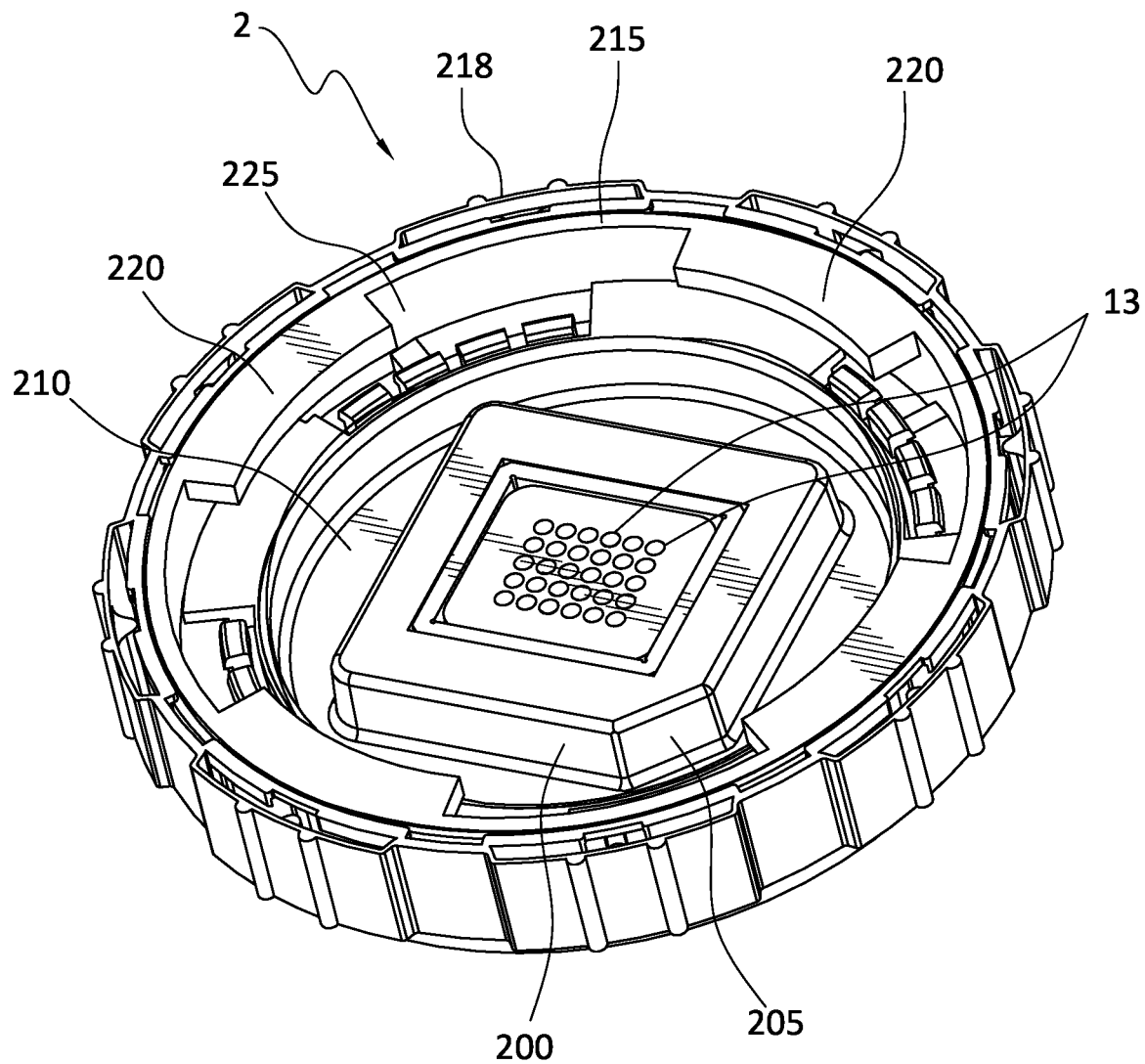
FIGS. 10 to 13 show the arm drape module, as used in the assembly of FIGS. 2 and 3.
Figure 11:
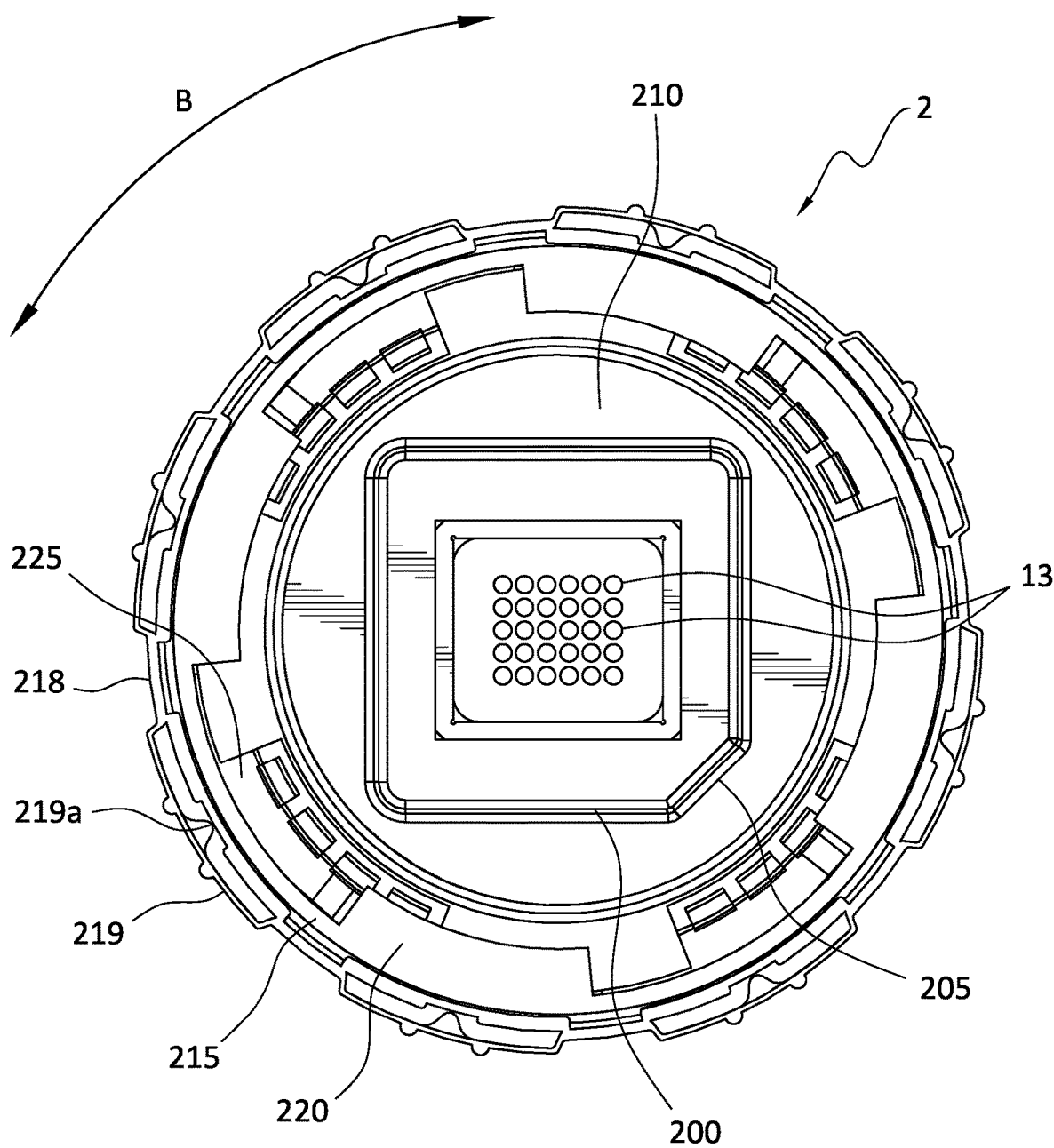
Figure 14:
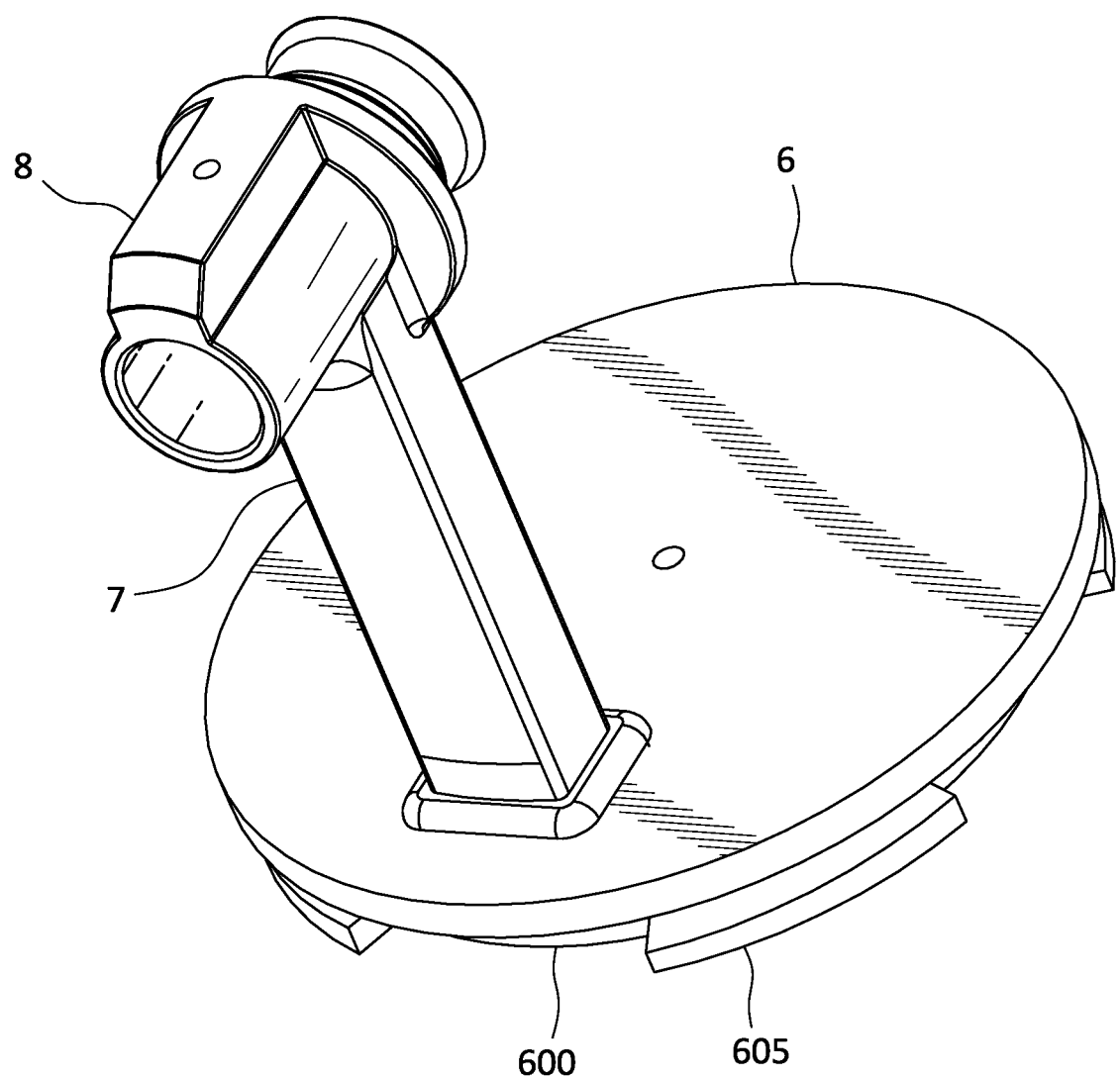
FIGS. 14 and 15 show a sterile reusable module that is reprocessable or disposable, as used in the assembly of FIG. 3.
Figure 18:
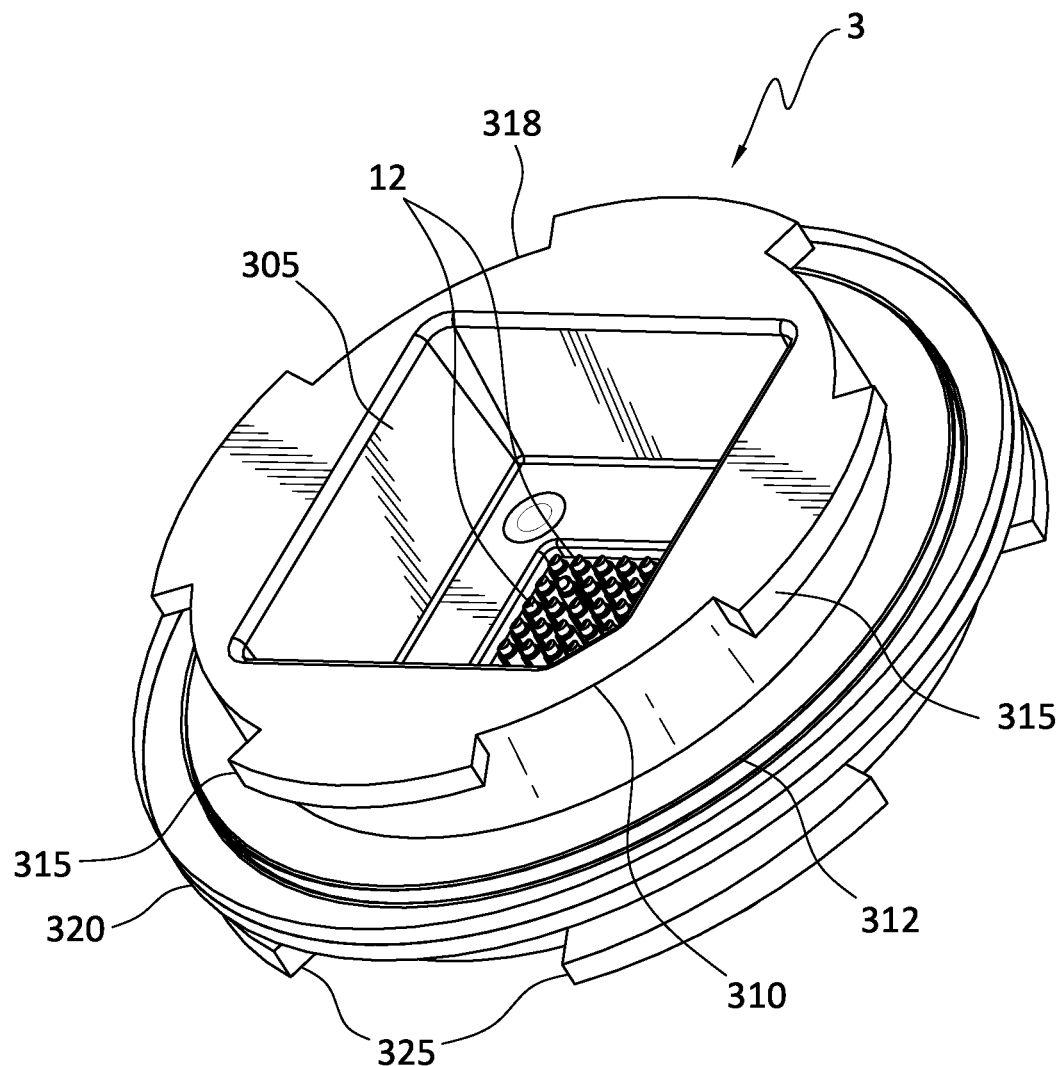
FIGS. 18 to 21 show the hand drape module, as used in the device of FIG. 1.

FIGS. 10 and 11 show a perspective view and a front plan view of a front surface of an arm drape module 2, respectively. The front surface of the arm drape module 2 is configured to be connected to:

end effector module 6, shown in FIG. 14; or
hand drape module 3, shown in FIG. 18.

As seen in FIG. 10, arm drape module 2 includes an elevated rectangular region 200, with electrical contacts 13 thereon. In some embodiments, a planar surface 205 may replace at least one corner of region 200, to facilitate and ensure the correct and unambiguous orientation of the connection between arm drape module 2 and hand drape module 3. Elevated region 200 is surrounded by a planar region 210. Elevated region 200 may have inclined surfaces, and may, for example, be a truncated cone or a truncated pyramid of 3 or more sides. The shape of elevated region 200 generally corresponds to the shape of elevated region 100.

Referring to FIG. 11, a rotatable inner ring 215 is mounted on arm mount module 1, and is configured to rotate reversibly in the direction of arrow B, between a locked position and an unlocked position. Rotatable inner ring 215 has a plurality of tabs 220, with spaces 225 between each pair of adjacent tabs. Tabs 120 serve as a first locking feature. In the unlocked position, spaces 225 in inner ring 215 are configured to receive tabs 605 on a rear surface of reusable or disposable end effector module 6 or tabs 325 on a rear surface of a hand drape module 3 (tabs 605 and 325, which serve as a second locking feature, are visible in FIGS. 15 and 21, respectively, and will be discussed later). In the locked position, tabs 220 in inner ring 215 are configured to be rotated in front of tabs 605 on end effector module 6, locking end effector module 6 to arm drape module 2. Outer ring 218, which serves as a third locking feature, is mounted on inner ring 215, and is normally freely rotatable relative to inner ring 215. However, referring to FIG. 11, elevated portions 219 of outer ring 218 have projections 219a on an inner surface thereof. A user may squeeze elevated portions 219 on opposing edges of outer ring 218, compressing elevated portions 219 radially inward toward inner ring 215 until projections 219a engage corresponding grooves on an outer surface of inner ring 215. Outer ring 218 may then be used to rotate inner ring 215 from an unlocked position to a locked position, or vice versa.

Figure 12:
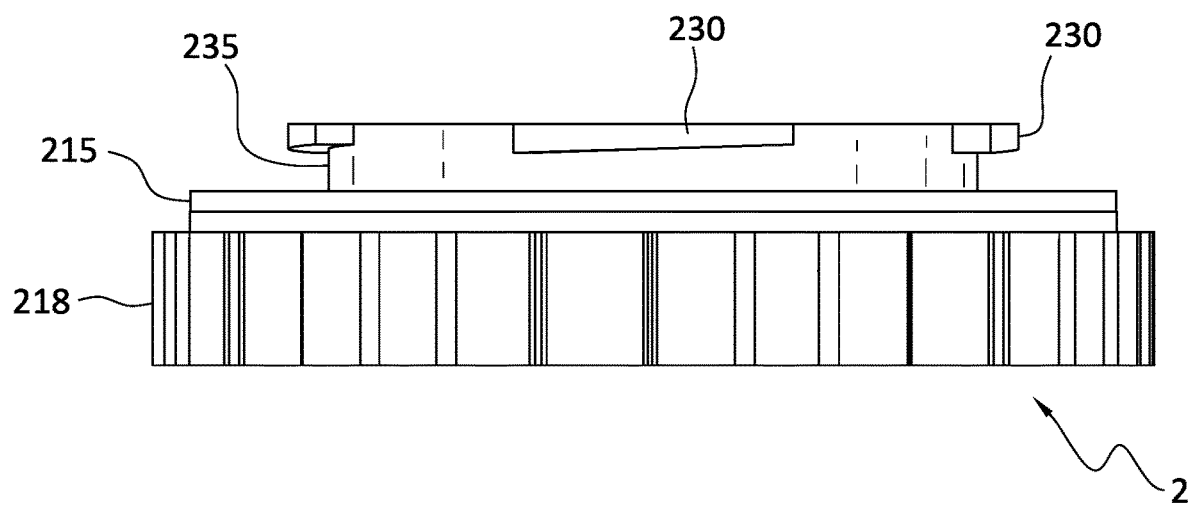

FIG. 12 shows a side view of arm drape module 2. Outer ring 218 and inner ring 215 are visible in FIG. 12. On the rear surface of arm drape module 2, a cylindrical projection 235 with tabs 230 thereon is visible. As discussed above, tabs 230 are configured to enter spaces 125 in the rotatable ring 115 on arm mount module 1, when rotatable ring 115 is in an unlocked position. When rotatable ring 115 is rotated into an locked position, tabs 120 in ring 115 are configured to be rotated in front of tabs 230 on arm drape module 2 to lock arm drape module 2 to arm mount module 1.

Figure 13:
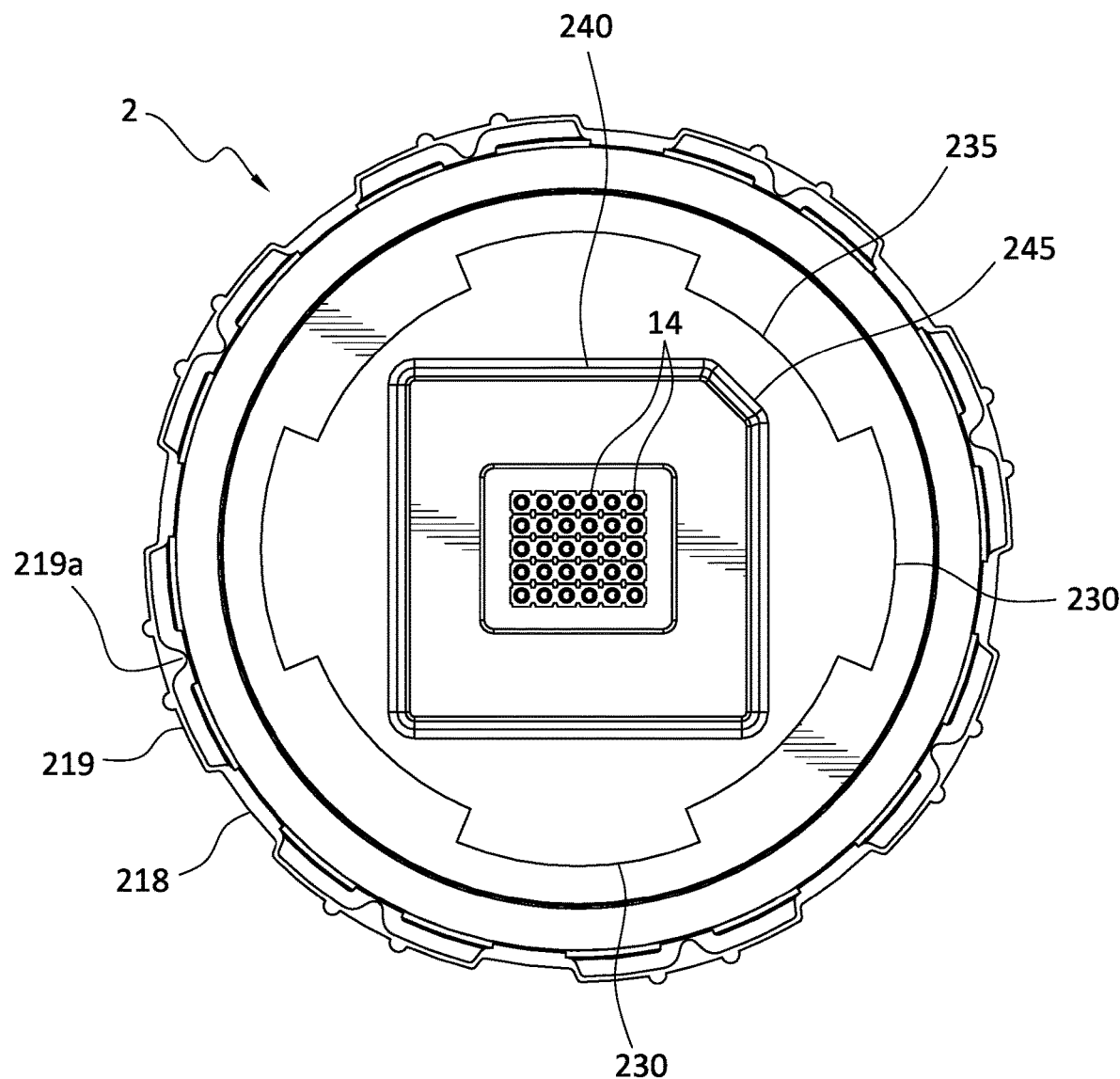

FIG. 13 shows a rear view of arm drape module 2. A depression 240 including electrical contacts 14 is visible in the rear surface of arm drape module 2, where depression 240 may have a truncated corner 245. Depression 240 has a shape which corresponds to the shape of elevated region 100 on the front surface of arm mount module 1, and is configured to fit over elevated region 100 when module 2 is connected to the front surface of module 1. In the embodiment of FIG. 13, the truncated corner 245 on depression 240 engages the planar surface 105 on a corner of region 100, ensuring that arm drape module 2 is connected to arm mount module 1 in a desired relative orientation. An inclined side surface of elevated region 100 supports a side surface of depression 240, and thereby carries the weight of arm drape module 2 and any end effector or other equipment attached thereto.

Figure 15:
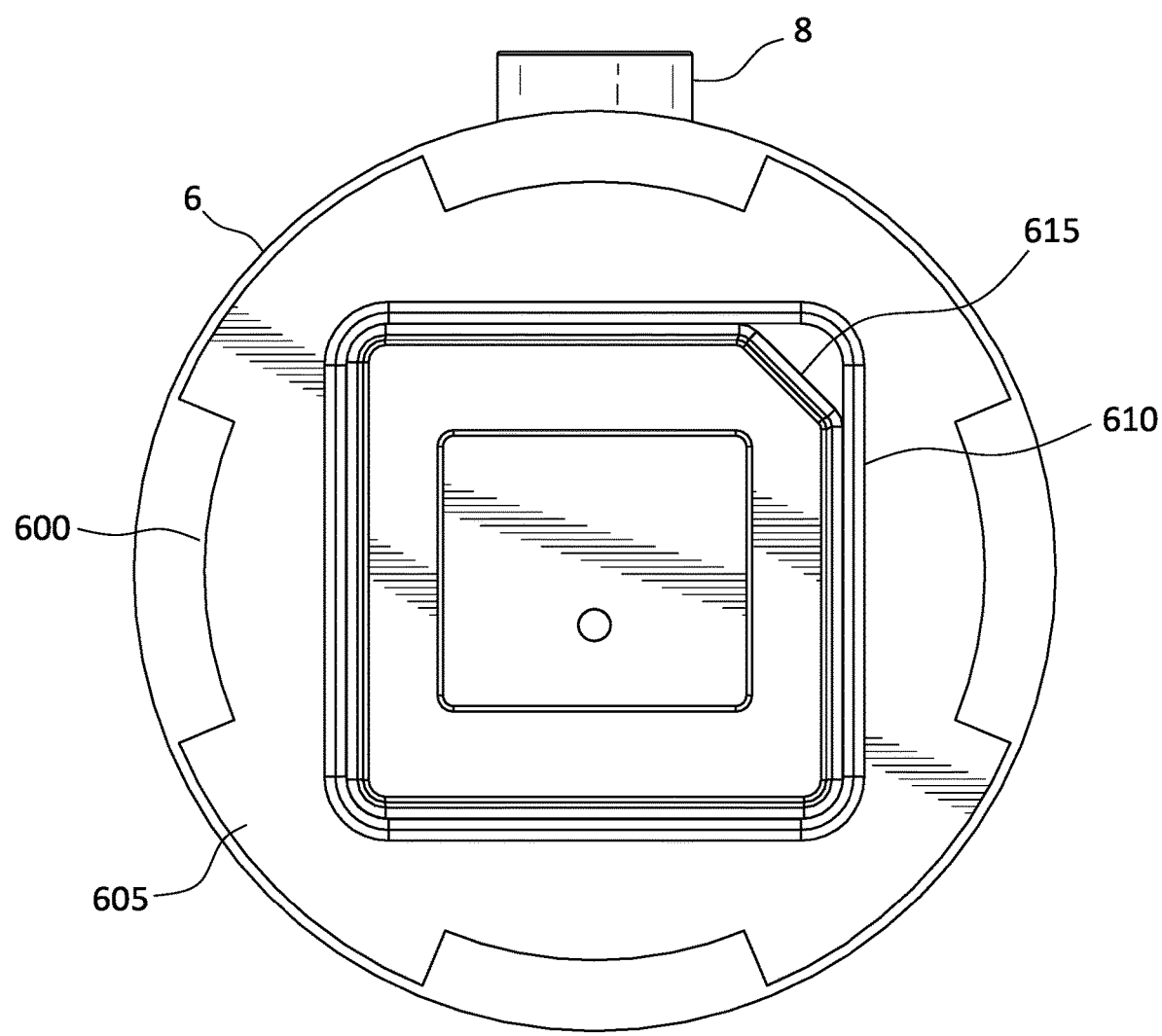

FIGS. 14 and 15 show a front perspective view and a rear view of a sterile reusable or disposable end effector module 6, respectively, where end effector module 6 is configured to be removably connected to arm drape module 2. As seen in FIGS. 14 and 15, the rear of end effector module 6 includes a set of tabs 605, extending radially from a cylindrical projection 600. A wall 610 in the rear of end effector module 6 defines an opening configured to fit over elevated region 200 on the front surface of arm drape module 2 when end effector module 6 is connected to the front surface of module 2. A truncated corner 615 on wall 610 engages the planar surface 205 on a corner of elevated region 200 on arm drape module 2, ensuring that end effector module 6 is connected to arm drape module 1 in a desired relative orientation. As discussed above, tabs 605 are configured to fit through spaces 225 in ring 215 when ring 215 on arm drape module 2 is in an unlocked position. When ring 215 on arm drape module 2 is in a locked position, tabs 220 in ring 215 are configured to be rotated in front of tabs 605 on end effector module 6, locking end effector module 6 to arm drape module 2. By reversing the locking procedure, arm drape module 2 may be unlocked from end effector module 6.

In the above discussion, multiple locking mechanisms are used. Arm drape module 2 is locked to end effector module 6 with a radial safety lock, where a rotatable outer ring 218 must be radially compressed to engage a rotatable inner ring 215. Arm mount module 1 is locked to arm drape module 2 with retractable pins or bearings 150 which engage a rotatable ring 115. However, in various embodiments, identical locking mechanisms may be used to connect arm mount module 1 to arm drape module 2, and to connect arm drape module 2 to end effector module 6. For example, arm drape module 2 may be locked to end effector module 6 with a first radial safety lock, and
arm mount module 1 may be locked to arm drape module 2 with a second radial safety lock.

Alternatively, arm mount module 1 may be locked to arm drape module 2 with a first set of retractable pins or bearings which engage a first rotatable ring 115, and
arm drape module 2 may be locked to end effector module 6 with a second set of retractable pins or bearings which engage a second rotatable ring.

In the above discussion, elevated regions 100 and 200, as well as depression 240 and wall 610 configured to engage these elevated regions, have been depicted as being rectangular, with an optionally truncated corner. However, other shapes may be envisioned, e.g., regular or irregular pentagonal, regular or irregular hexagonal, cylindrical, or elliptical. In some embodiments elevated regions 100 and 200 and the corresponding depressions may be cylindrical, with a planar surface on one side or on an upper surface, where the planar surfaces interact to maintain a desired orientation between connected modules. Preferably, the elevated regions or projections are weight-bearing. The elevated regions or projections, as well as the depressions, may have sides which sloped, relative to an axis of the projections or depressions. The outer surface of elevated regions 100 and 200, as well as the inner surface of depression 240 and wall 610, may be frustopyramidal or frustoconical.

Figure 16:
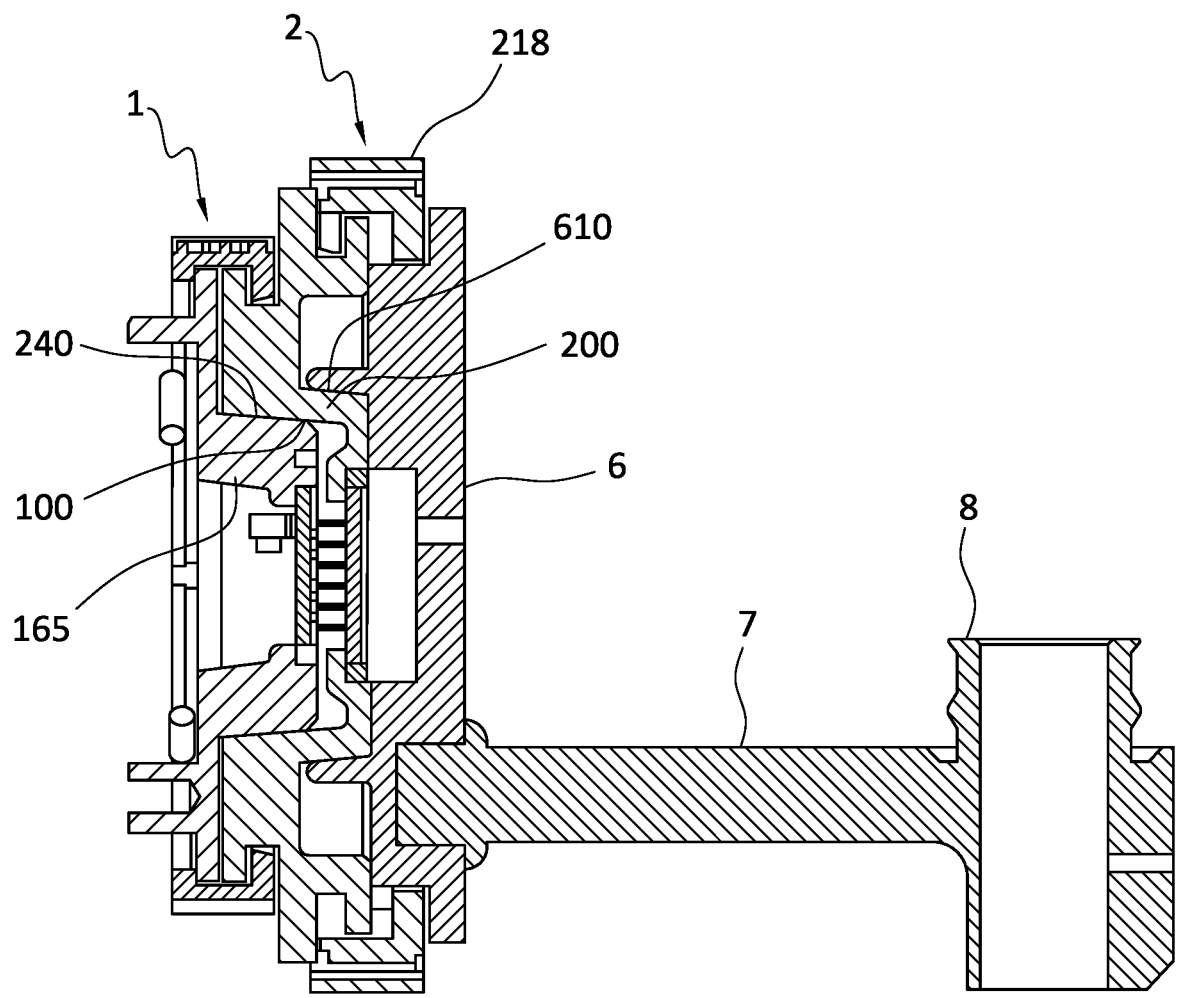
FIG. 16 shows a cross section of the system of FIG. 3, including an arm mount module, an arm drape module, and a sterile reprocessable or disposable module.

FIG. 16 shows a cross sectional view showing how arm mount module 1, arm drape module 2, and end effector module 6 are connected together. As seen in FIG. 16, arm mount module 1 includes a frustoconical or frustopyramidal wall with a rear surface defining indentation 165, and a front surface defining elevated rectangular region 100. Arm drape module 2 is fitted to arm mount module 1, with depression 240 in the rear surface of arm drape module 2 engaging elevated region 100 in the front surface of arm mount module 1. End effector module 6 has a wall 610 on its rear surface, where wall 610 defines an opening configured to receive elevated rectangular region 200 on arm drape module 2.

Figure 17:
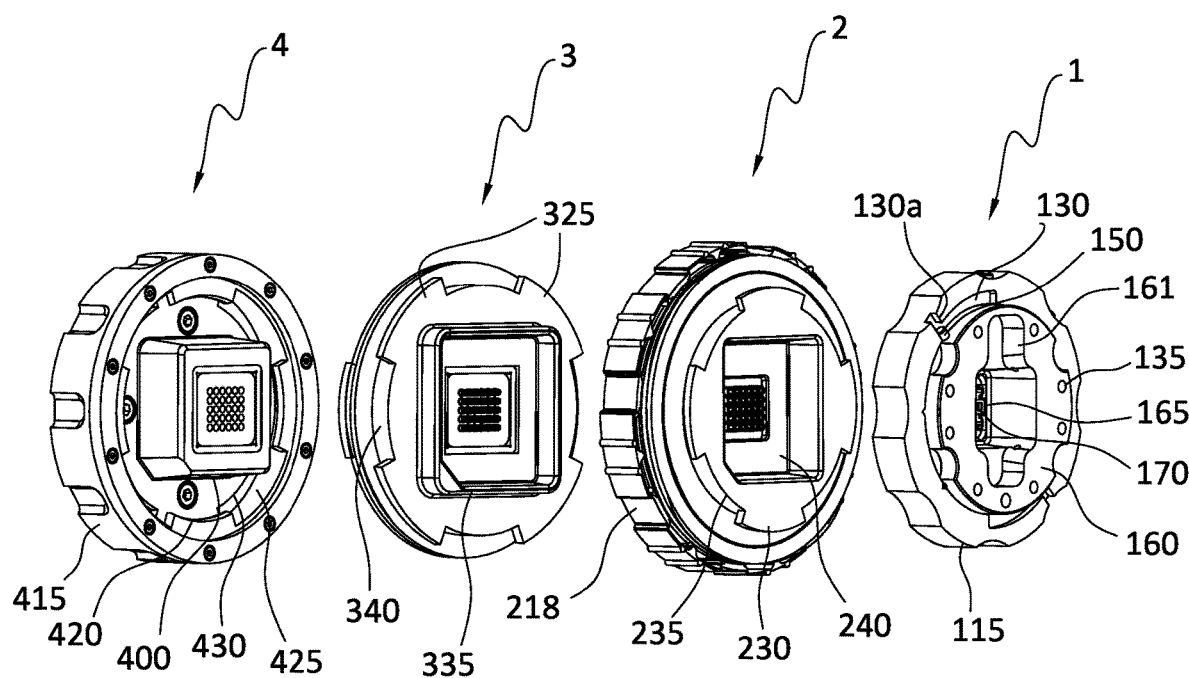
FIG. 17 shows an exploded view of the device of FIG. 1.

FIG. 17 shows an exploded view of the system for connecting a robot arm to an end effector of FIG. 1. Arm mount module 1 is substantially similar to the arm mount module 1 as depicted in FIGS. 6 to 9, and will not be further described here. Arm drape module 2 is substantially similar to the arm drape module 1 as depicted in FIGS. 10 to 13, and will also not be further described here. As seen in FIG. 17, a hand drape module 3 is used to connect a hand mount module 4 to arm drape module 2. An end effector device, e.g., a drill or saw, may then be connected with bolts or screws to hand mount module 4.

FIGS. 18 to 21 show hand drape module 3, where a rear surface of hand drape module 3 (shown in FIG. 21) is configured to be connected to arm drape module 2.

Figure 19:
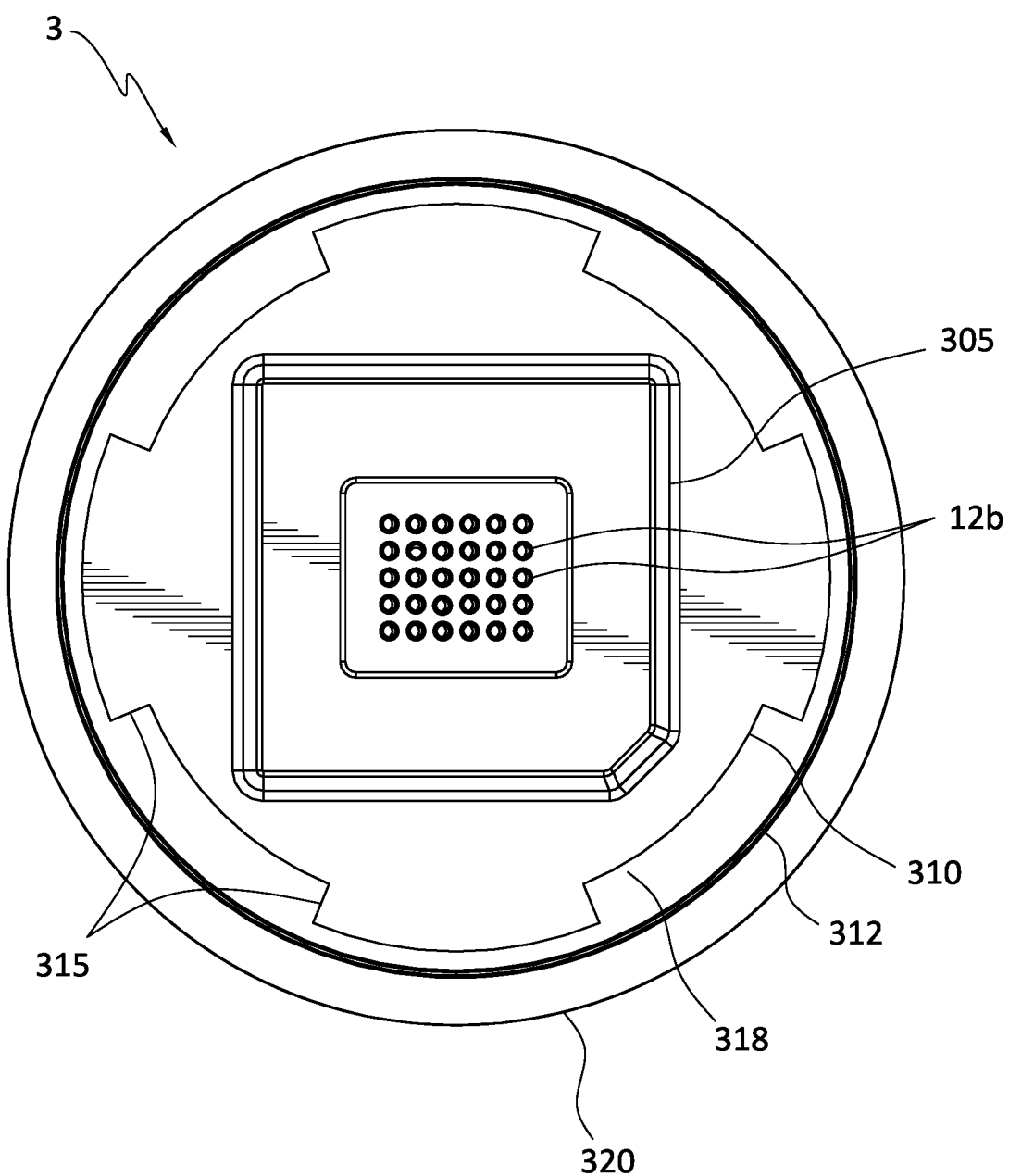
Figure 22:
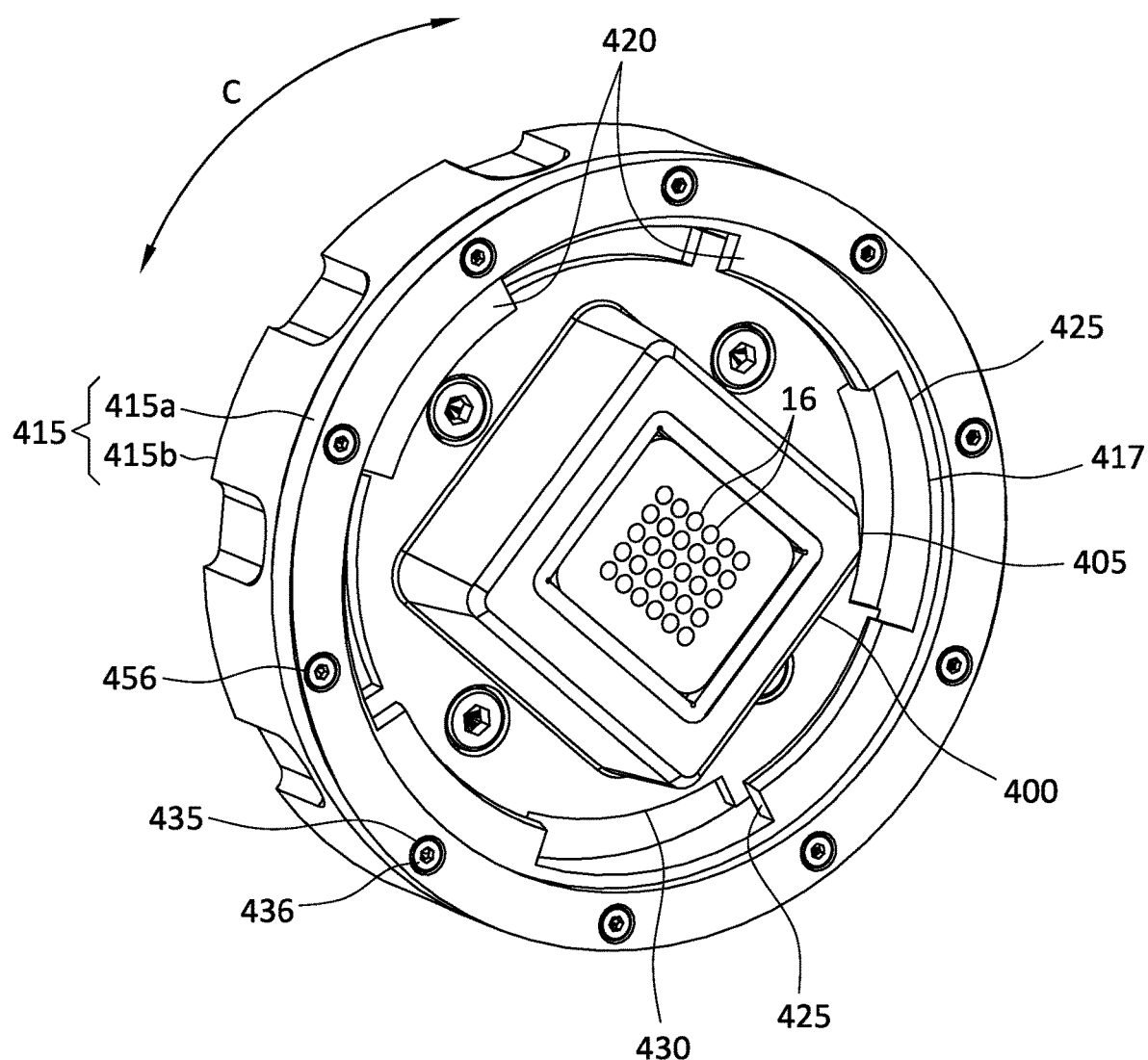
FIG. 22 shows the hand mount module, as used in the device of FIG. 1.

FIGS. 18 and 19 show a perspective view and a front view of a hand drape module 3, respectively. The front surface of the hand mount module 3 is configured to be connected to an end effector. As seen in FIGS. 18 and 19, hand drape module 3 has a planar front surface 312 with a cylindrical projection 310 thereon. A depression 305, which may be shaped as a regular or irregular polygon, e.g., a square, a rectangle, a rectangle with a truncated corner, a cylinder, a cylinder with a flattened side, etc., is positioned on the upper surface of cylindrical projection 310. Electrical contacts 12b are positioned on a lower surface of depression 305. On the upper surface of cylindrical projection 310, tabs 315 are positioned, with spaces 318 between each pair of tabs 315. As discussed below, tabs 315 serve as a second locking feature, and are configured to enter spaces 425 in a rotatable ring 415 on hand mount module 4, as seen in FIG. 22. A flange 320 may optionally extend radially from an outer edge of planar surface 312.

Figure 20:
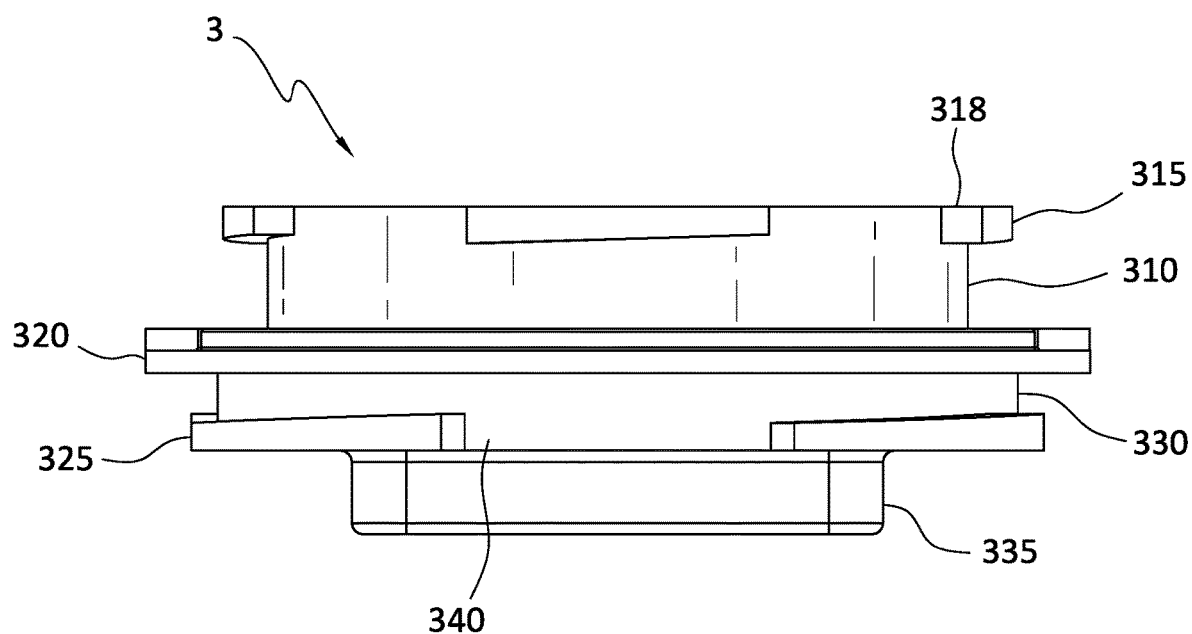
Figure 21:
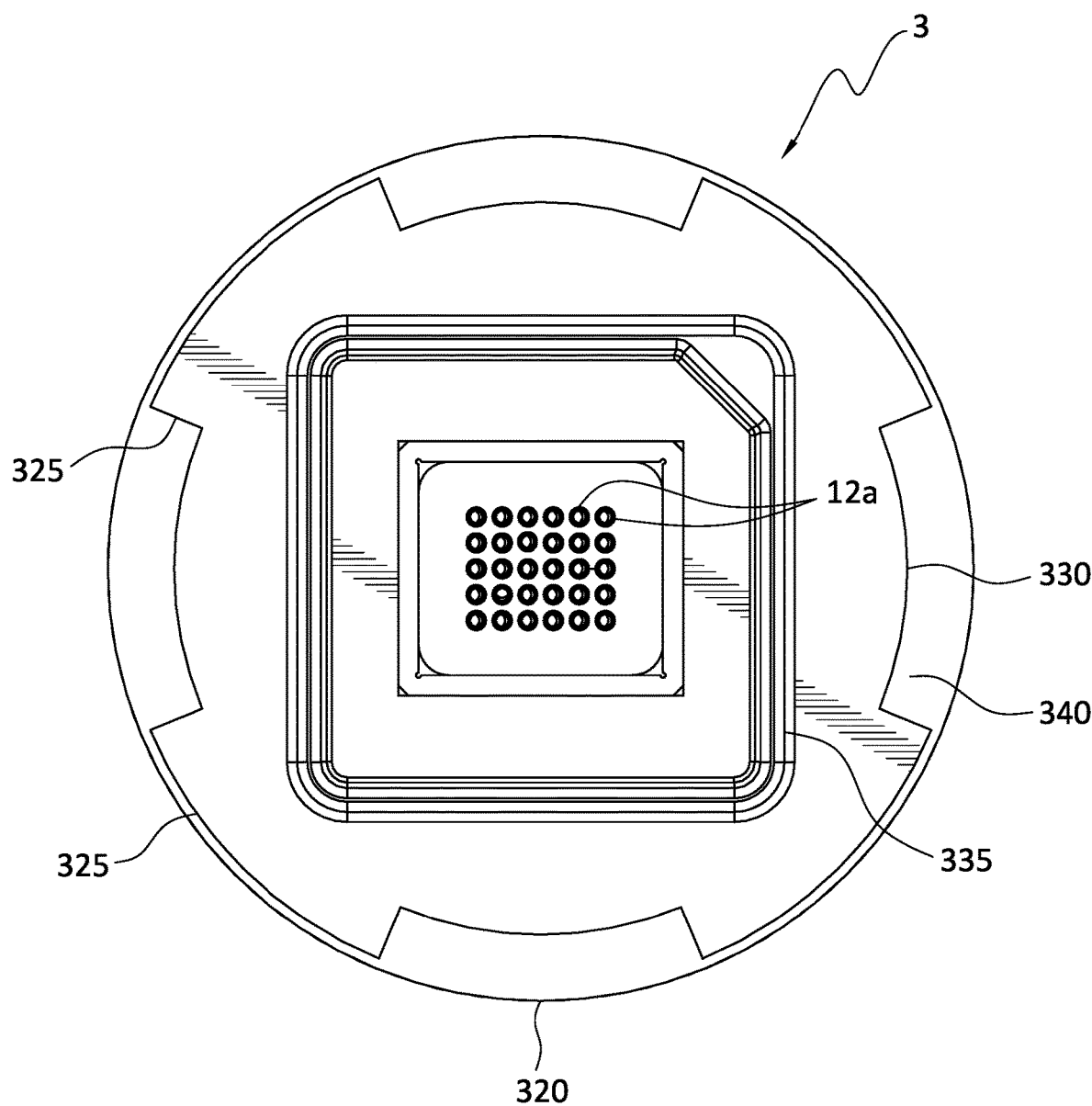

FIG. 20 shows a side view of hand drape module 3. Projection 310, with tabs 315 thereon, is visible on a front side of flange 320 in FIG. 20. A second projection 330, with tabs 325 extending from projection 330, is visible on a rear side of flange 320. Tabs 325 are also designed to serve as a second locking feature. Spaces 340 are visible between each pair of tabs 315. FIG. 21 shows a rear view of hand drape module 3. A wall 335 defines an opening configured to receive elevated rectangular region 200 on arm drape module 2. Electrical contacts 12a are configured to make electrical contact with electrical contacts 13 on arm drape module 2.

Hand drape module 3 is configured to be removably connected to arm drape module 2. Tabs 325 on hand drape module 3 are configured to fit through spaces 225 in inner ring 215 on arm drape module 2, when inner ring 215 is in an unlocked position. When inner ring 215 on arm drape module 2 is rotated into a locked position, tabs 220 in inner ring 215 serve as a first locking feature, and are configured to be rotated in front of tabs 325 on hand drape module 3, locking hand drape module 3 to arm drape module 2. By reversing the locking procedure, hand drape module 3 may be unlocked from arm drape module 2.

FIG. 22 shows hand mount module 4. Hand mount module 4 is configured to be connected to an end effector, e.g., a saw or drill. A projection 400, which may be shaped as a rectangle with a truncated corner 405, extends from a rear of hand mount module 4, and is configured to be received within depression 305 in the front of hand drape module 3. Electrical contacts 16 on projection 400 are configured to make electrical contact with electrical contacts 12b on hand drape module 3. Contacts 16 are generally flush with an upper surface of elevated region 400, allowing easy cleaning, disinfection and/or sterilization prior to use. Hand mount module 4 contains a plurality of arcuate spaces 430 in its periphery. A rotatable outer ring 415 is mounted on hand mount module 4, and is configured to rotate reversibly from a first position to a second position. Outer ring 415 is constructed of a forward portion 415b and a rear portion 415a, screwed together with screws 456. A rotatable inner ring 417 is biased toward a rear surface of outer ring 415, i.e., towards ring portion 415a, but may be reversibly compressed in a forward direction toward ring portion 415b. Rotatable inner ring 417 has a plurality of tabs 420, with spaces 425 between each pair of adjacent tabs. Tabs 420 on inner ring 417 serve as a first locking feature. Referring to FIG. 22, ring 417 on hand mount module 4 is rotatable reversibly in the direction of arrow C, between a locked position and an unlocked position. In the unlocked position, spaces 425 in ring 417 are configured to receive tabs 315 on a front surface of hand drape module 3 (tabs 315, a second locking feature, are visible in FIG. 18, discussed above). In the locked position, tabs 420 in ring 417 are configured to be rotated in front of tabs 315 on hand drape module 3, locking hand drape module 3 to hand mount module 4.

Figure 23:
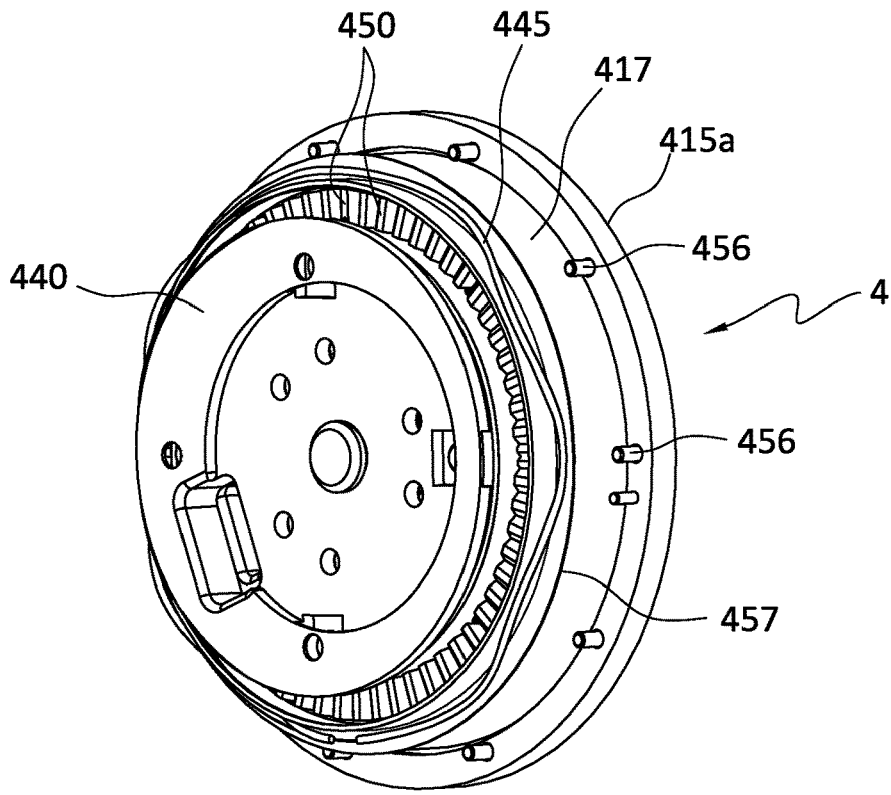
FIGS. 23 and 24 show a locking mechanism suitable for use in the hand mount module, as seen in the device of FIG. 1.
Figure 24:
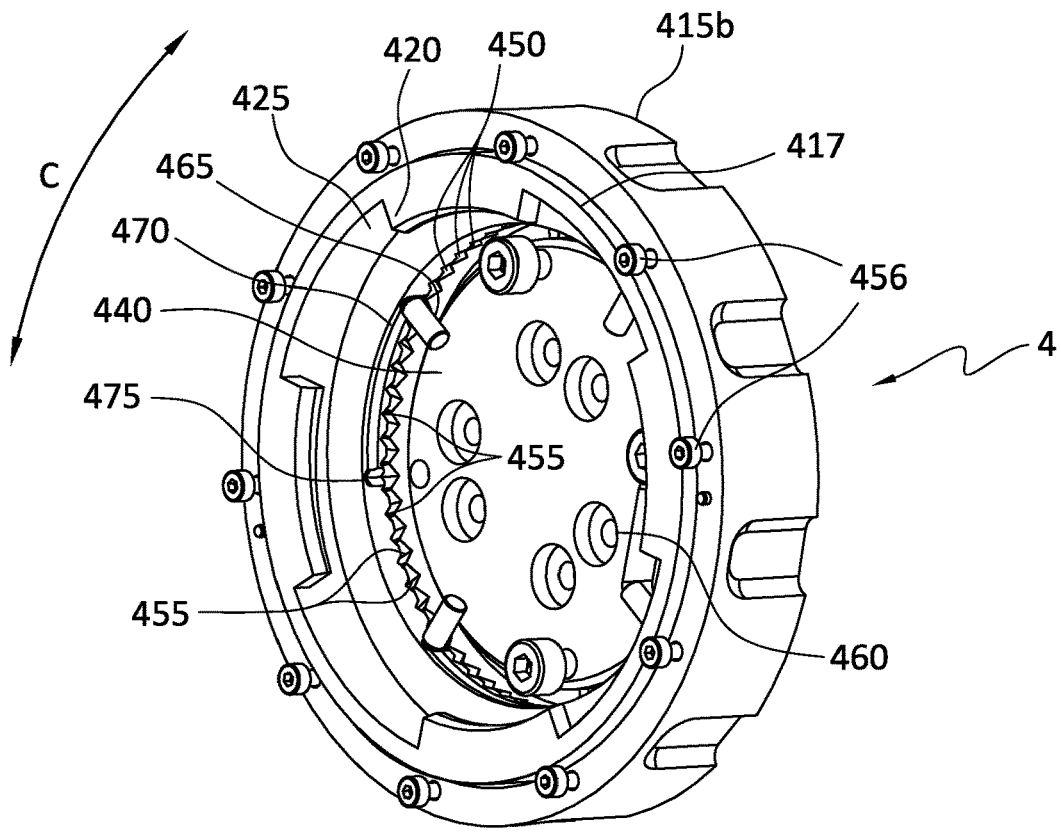

FIG. 23 shows a front view of hand mount module 4, while FIG. 24 shows a rear view of hand mount module 4. In FIG. 23, the forward portion 415b of outer ring 415 is removed for clarity. A rear surface of inner ring 417 contacts a forward surface of the rear portion of outer ring 415. A spring 445 is positioned between a forward surface 457 of inner ring 417 and the forward portion 415b of outer ring 415, biasing inner ring 417 away from the forward portion 415b of outer ring 415. The spring 445 may maintain a distance between inner ring 417 and the forward portion 415b of outer ring 415, without causing inner ring 417 to make contact with rear portion 415a of outer ring 415. Spring 445, in an uncompressed state, prevents engagement between a row of teeth 450 on the forward surface of inner ring 417, shown in FIGS. 23 and 24, and a row of teeth 455 on the on the forward portion 415b of outer ring 415, shown in FIG. 24, allowing outer ring 415 to rotate freely relative to inner ring 417.

When hand mount module 4 is pressed onto hand drape module 3, a force applied by the operator to a rear surface of outer ring 415 exceeds the force applied by spring 445, causing inner ring 417 to move toward the forward portion 415b of outer ring 415. The resulting compression of spring 445 allows inner ring 417 to move axially forward, relative to a forward surface 440 of module 4 (generally corresponding to front plate 17 of FIG. 4). As inner ring 417 moves axially forward, the row of teeth 450 on the forward surface of inner ring 417 also moves in an axial direction.

FIG. 24 shows a rear view of hand mount module 4. In FIG. 24, the rear portion 415a of outer ring 415 and the plate containing projection 400 are removed for clarity. Inner ring 417 and the forward portion 415b of outer ring 415 are axially spaced from each other. As discussed above, when hand mount module 4 is pressed onto hand drape module 3, spring 445 (not visible in FIG. 24) may be compressed, allowing the inner ring 417 to move axially forward.

As inner ring 417 moves axially forward, teeth 450 on the forward surface of inner ring 417 may engage teeth 455 on the forward portion 415b of outer ring 415. Engagement of teeth 450 and 455 must be initiated to fix and/or release ring 415, relative to ring 417. Before teeth 450 engage teeth 455, rotation of the outer ring 415 is independent of the inner ring 417, and does not cause rotation of tabs 420. Once teeth 450 engage teeth 455, the outer ring 415 and the inner ring 417 rotate reversibly as a unit in the direction of arrow C, causing rotation of tabs 420. Teeth 450 thus serve as a third locking feature. When hand mount module 4 is positioned on hand drape module 3, the outer ring 415 of hand mount module 4 is pressed or pulled onto the inner ring 417 of hand mount module 4 until teeth 450 engage teeth 455. The outer ring 415 is then rotated until tabs 420 in ring 417 are positioned in front of tabs 315 on hand drape module 3, locking hand mount module 4 to hand drape module 3. Hand mount module is released, and spring 445 biases ring 417 axially away from a front of module 4, causing teeth 450 and teeth 455 to disengage. Once the teeth have disengaged, rotation of the outer ring 415 does not affect tabs 420. By reversing the locking procedure, hand mount module 4 may be unlocked from hand drape module 3. If rotation of the outer ring 415 is attempted prior to proper engagement of teeth 450 and 455, then outer ring 415 and inner ring 417 will not rotate as a unit, and hand mount module 4 and hand drape module 3 will not properly lock together.

As seen in FIG. 24, hand mount module 4 includes pins or bearings 465. The outer ring 415 and the inner ring 417, when teeth 450 and teeth 455 are engaged, rotate reversibly as a unit in the direction of arrow C. Outer surfaces of pins or bearings 465 move within grooves 470, limiting rotation of ring 417 to movement between a first unlocked position and a second locked position. When ring 417 enters its second locked position, pins or bearings 465 may enter detents 475, holding ring 417 in the locked position. As pins or bearings 465 enter detents 475 there may be tactile or auditory feedback, indicating that hand drape module 3 and hand mount module 4 are locked together.

Figure 25:
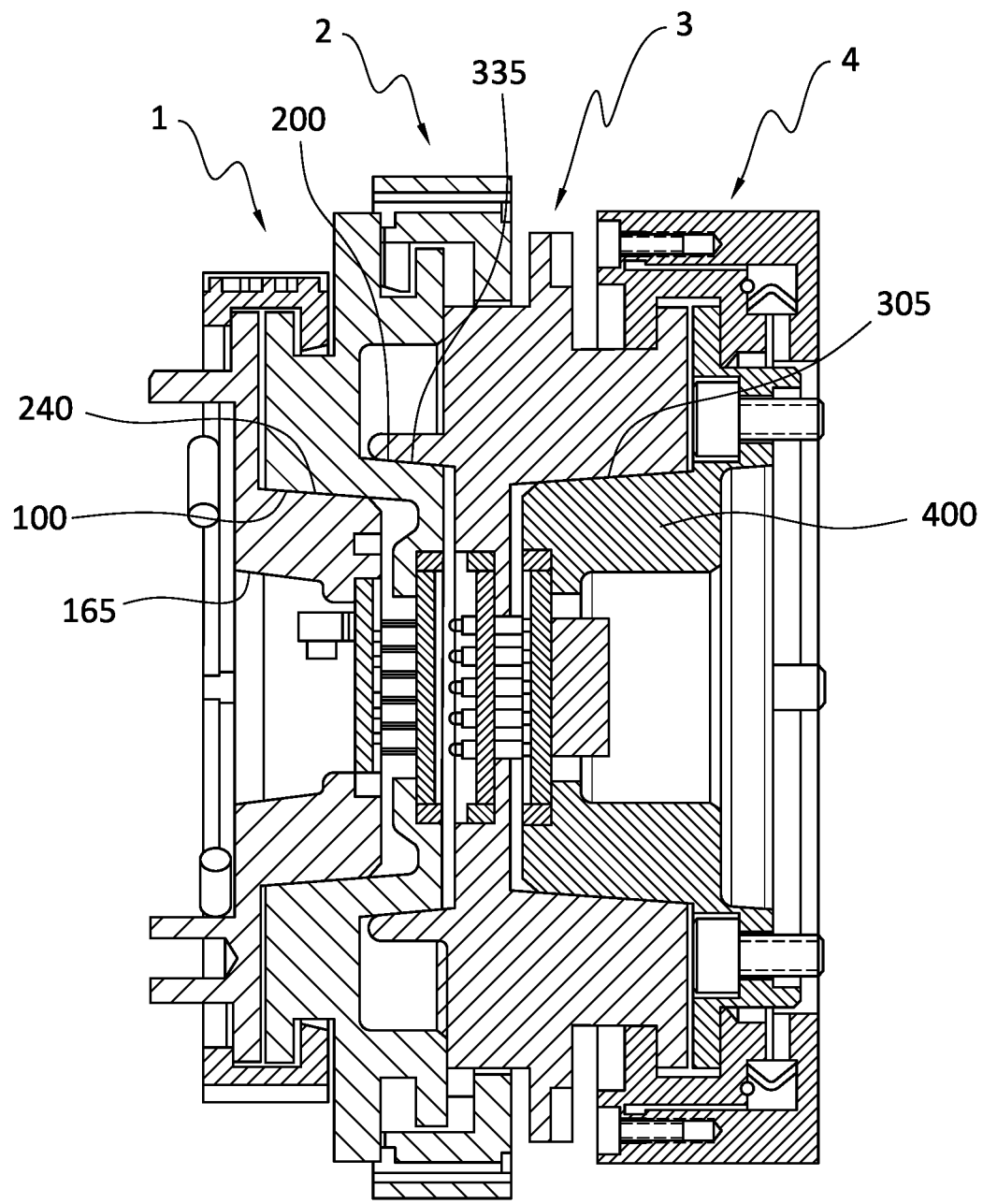
FIG. 25 shows a cross section of the system of FIG. 1, including an arm mount module, an arm drape module, a hand drape module, and a hand mount module.

FIG. 25 shows a cross sectional view showing how arm mount module 1, arm drape module 2, hand drape module 3 and hand mount module 4 are connected together. As seen in FIG. 25, arm mount module 1 includes a frustoconical or frustopyramidal wall with a rear surface defining indentation 165, and a front surface defining elevated rectangular region 100. Arm drape module 2 is fitted to arm mount module 1, with depression 240 in the rear surface of arm drape module 2 engaging elevated region 100 of arm mount module 1. Hand drape module 3 has a wall 335 on its rear surface, where wall 335 defines an opening configured to receive elevated rectangular region 200 on arm drape module 2. Hand drape module 3 has a depression 305 on its front surface, which is configured to engage projection 400 on the rear of hand mount module 4. Arm mount module 1 is configured to be temporarily or permanently fixed to a robot arm 5. Hand mount module 4 is configured to be temporarily or permanently fixed to an end effector, e.g., a medical saw or drill. In some embodiments, hand mount module 4 may be an end effector.

In various embodiments, the arm mount module 1, arm drape module 2, hand drape module 3 and hand mount module 4 may be provided as a kit and used to connect an end effector to a robot arm, with the end effector being connected to hand mount module 4 and the robot arm being connected to the arm mount module.

In some embodiments, arm drape module 2 and hand drape module 3 are provided as a kit, with:
  arm drape module 2 being configured to be connected to an arm mount module provided as part of a robot arm, and
  hand drape module 3 being configured to be connected to a hand mount module provided as part of an end effector.

In various embodiments, arm mount module 1 and hand mount module 4 may be provided as a kit, and used to retrofit an existing robot arm and end effector for use in a system of FIG. 25. Arm drape module 2 and hand drape module 3 may also be provided as disposable components of a kit, and used to connect the retrofitted end effector to the retrofitted robot arm.

In the above discussion, multiple locking mechanisms are used. Arm drape module 2 is locked to hand drape module 3 with a radial safety lock, where a rotatable outer ring 218 must be radially compressed to engage a rotatable inner ring 215. Arm mount module 1 is locked to arm drape module 2 with pins or bearings 156 which engage notches 157 and 158 on rotatable ring 115. Hand mount module 4 is locked to hand drape module 3 with an axial safety lock, where two axially spaced rings with teeth configured to engage when modules 3 and 4 are pressed together. However, in various embodiments, identical locking mechanisms may be used to connect arm mount module 1 to arm drape module 2, to connect arm drape module 2 to hand drape module 3, and to connect hand mount module 4 to hand drape module 3. For example,
  arm drape module 2 may be locked to hand drape module 3 with a first radial safety lock,
  arm mount module 1 may be locked to arm drape module 2 with a second radial safety lock, and
  hand mount module 4 may be locked to hand drape module 3 with a third radial safety lock.
Alternatively,
  arm mount module 1 may be locked to arm drape module 2 with a first set of retractable pins or bearings which engage a first rotatable ring 115,
  arm drape module 2 may be locked to hand drape module 3 with a second set of retractable pins or bearings which engage a second rotatable ring, and
  hand mount module 4 may be locked to hand drape module 3 with a second set of retractable pins or bearings which engage a third rotatable ring. Similarly, the system may be constructed with a set of three axial safety locks.

Additionally, the various locking mechanisms disclosed herein may be interchanged if desired, and used in any desired combination. In the above discussion, arm drape module 2 may be locked to hand drape module 3 with a radial safety lock. If desired, arm drape module 2 may be locked to hand drape module 3 with an axial safety lock, or with a set of retractable pins or bearings which engage a rotatable ring.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:
1. A system for removably connecting an end effector to a robot arm, comprising:
  an arm mount module having a front surface and a rear surface,
    wherein the arm mount module is configured to be connected to a robot arm;

an arm drape module having a front surface and a rear surface,
    wherein the rear surface of the arm drape module is configured to be removably connected to the front surface of the arm mount module by a first locking mechanism; and
a third module configured to be removably connected to the arm drape module by a second locking mechanism, and to be removably connected to the end effector, wherein:
    at least one of the arm drape module and the third module comprises a flexible drape, the flexible drape being configured to cover the robot arm or the end effector;
    a first module comprises a depression, the first module being one of the arm mount module, the arm drape module, and the third module; and
    the depression is configured to receive a corresponding weight-bearing projection on a second module connected to the first module, the second module being a different one of the arm mount module, the arm drape module, and the third module.

2. A system for removably connecting an end effector to a robot arm, comprising:
an arm mount module having a front surface and a rear surface,
    wherein the arm mount module is configured to be connected to a robot arm;
an arm drape module having a front surface and a rear surface,
    wherein the rear surface of the arm drape module is configured to be removably connected to the front surface of the arm mount module by a first locking mechanism; and
a third module configured to be removably connected to the arm drape module by a second locking mechanism, and to be removably connected to the end effector,
    wherein at least one of the arm drape module and the third module comprises a flexible drape, the flexible drape being configured to cover the robot arm or the end effector;
    wherein:
        the arm mount module comprises a weight-bearing frustoconical or frustopyramidal projection on the front surface thereof; and
        the arm drape module comprises a corresponding frustoconical or frustopyramidal depression on the rear surface thereof; and
        the frustoconical or frustopyramidal depression on the arm drape module is configured to receive the weight-bearing frustoconical or frustopyramidal projection on the arm mount module.

3. The system of claim 2, wherein:
the arm drape module comprises a weight-bearing frustoconical or frustopyramidal projection on the front surface thereof; and
the third module comprises a corresponding frustoconical or frustopyramidal depression on the rear surface thereof;
wherein the frustoconical or frustopyramidal depression on the third module is configured to receive the weight-bearing frustoconical or frustopyramidal projection on the arm mount module.

4. The system of claim 2, wherein:
the arm mount module comprises a frustopyramidal projection on the front surface thereof, wherein an upper surface of the frustopyramidal projection is planar; and the arm drape module comprises a corresponding frustopyramidal depression on the rear surface thereof, wherein an upper surface of the frustopyramidal depression is planar;
wherein the frustoconical or frustopyramidal depression on the arm drape module is configured to engage the weight-bearing frustoconical or frustopyramidal projection on the arm mount module so as to ensure a desired alignment between the arm mount module and the arm drape module.

5. The system of claim 2, further comprising a means for transmitting a signal and/or power to, or receiving a signal and/or electrical power from, the end effector, the means for transmitting or receiving a signal and/or electrical power comprising:
an electrical connector configured to make electrical contact with the robot arm on the rear surface of the arm mount module;
a plurality of first electrical contacts on the front surface of the arm mount module, the first electrical contacts being in electrical contact with the electrical connector;
a plurality of second electrical contacts on the arm drape module, the second electrical contacts being configured to engage the planar first electrical contacts;
a plurality of third electrical contacts on the arm drape module, the third electrical contacts being in electrical contact with the second electrical contacts;
a plurality of fourth electrical contacts on the third module, the fourth electrical contacts being configured to engage the third electrical contacts; and
a plurality of fifth electrical contacts on the third module, the fifth electrical contacts being in electrical contact with the fourth electrical contacts;
wherein the electrical connector, the first electrical contacts, the second electrical contacts, the third electrical contacts, the fourth electrical contacts and the fifth electrical contacts establish a signal and power transmission pathway between the robot arm and the end effector.

6. The system of claim 2, wherein the third module comprises a reusable or disposable module with a base configured to be removably connected to the arm drape module, and an arm having a mount configured to removably receive the end effector;
the arm drape module comprises the flexible drape; and
the flexible drape is configured to cover the robot arm.

7. The system of claim 2, wherein:
the system further comprises a hand mount module connected to the end effector;
the third module is a hand drape module configured to be removably connected to the arm drape module by the second locking mechanism, and to be removably connected to the hand mount module by a third locking mechanism; and
the arm drape module and the hand drape module are sterile or made of sterilizable materials.

8. A system for removably connecting an end effector to a robot arm, comprising:
an arm mount module having a front surface and a rear surface,
    wherein the rear surface of the arm mount module is configured to be connected to a robot arm;
an arm drape module having a front surface and a rear surface, wherein the rear surface of the arm drape module is configured to be removably connected to the front surface of the arm mount module by a first locking mechanism;

a hand drape module having a front surface and a rear surface, wherein the rear surface of the hand drape module is configured to be removably connected to the front surface of the arm drape module by a second locking mechanism; and a hand mount module having a front surface and a rear surface, wherein:

the rear surface of the hand mount module is configured to be removably connected to the front surface of the hand drape module by a third locking mechanism, and the front surface of the hand mount module comprises the end effector, or is configured to be connected to the end effector;

wherein at least one of the first locking mechanism, the second locking mechanism, and the third locking mechanism comprises:

a first ring mounted on a first module, the first ring being rotatable from an unlocked position to a locked position, the first ring comprising a first locking feature, wherein the first module is selected from the group consisting of the arm mount module, the arm drape module, the hand drape module, and the hand mount module; and a second locking feature on a second module, the second module being removably connected to the first module, wherein the first locking feature engages the second locking feature when the first ring is in the locked position.

9. The system of claim 8, wherein:
the arm drape module is sterile or made of a sterilizable material; and
the arm drape module comprises a drape made of a sterile material, the drape being configured to cover the arm mount module and the robot arm.

10. The system of claim 8, wherein:
the hand drape module is sterile or made of a sterilizable material; and
the hand drape module comprises a drape made of a sterile material, the drape being configured to cover the hand mount module and the end effector.

11. The system of claim 8, wherein:
the arm drape module and the hand drape module are sterile or made of a sterilizable material;
the arm drape module comprises a first drape made of a sterile material, the first drape being configured to cover the arm mount module and the robot arm; and
the hand drape module comprises a second drape made of a sterile material, the second drape being configured to cover the hand mount module and the end effector.

12. The system of claim 8, further comprising a means for transmitting a signal and/or electrical power to, or receiving a signal and/or electrical power from, the end effector, the means for transmitting or receiving a signal and/or electrical power comprising:

an electrical connector configured to make electrical contact with the robot arm on the rear surface of the arm mount module;

a plurality of first electrical contacts on the front surface of the arm mount module, the first electrical contacts being in electrical contact with the electrical connector;

a plurality of second electrical contacts on the arm drape module, the second electrical contacts being configured to engage the planar first electrical contacts;

a plurality of third electrical contacts on the arm drape module, the third electrical contacts being in electrical contact with the second electrical contacts;

a plurality of fourth electrical contacts on the hand drape module, the fourth electrical contacts being configured to engage the third electrical contacts;

a plurality of fifth electrical contacts on the hand drape module, the fifth electrical contacts being in electrical contact with the fourth electrical contacts;

a plurality of sixth electrical contacts on the hand mount module, the sixth electrical contacts being configured to engage the fifth electrical contacts; and wherein the electrical connector, the first electrical contacts, the second electrical contacts, the third electrical contacts, the fourth electrical contacts the fifth electrical contacts and the sixth electrical contacts establish a signal and/or electrical power transmission pathway between the robot arm and the end effector.

13. The system of claim 8, further comprising a means for transmitting a mechanical, hydraulic, or pneumatic power from the robot arm to the end effector.

14. The system of claim 8, wherein at least one of the first locking mechanism, the second locking mechanism, and the third locking mechanism further comprises:

a third locking feature, wherein:
the third locking feature is configured to engage the first ring, and
the third locking feature either:
prevents rotation of the first ring when the third locking feature engages the third ring, or
allows rotation of the first ring only when the third locking feature engages the third ring.

15. The system of claim 8, wherein at least one of the first locking mechanism, the second locking mechanism, and the third locking mechanism comprises:

the first ring mounted on the first module, wherein the first locking feature on the first ring comprises a plurality of inwardly directed flanges having spaces therebetween; and the second locking feature on the second module, wherein the second locking feature comprises a plurality of outwardly directed flanges on the second module, wherein:

the outwardly directed flanges on the second module are configured to be aligned with the spaces between the inwardly directed flanges on the first ring on the first module when the first ring on the first module is in the unlocked position; and the outwardly directed flanges on the second module are configured to be aligned with the inwardly directed flanges on the first ring on the first module when the first ring on the arm mount module is in the locked position.

16. The system of claim 15, wherein:
the first module comprises a retractable pin or bearing,
the first ring mounted on the first module comprises a hole configured to receive the retractable pin or bearing, and
the retractable pin or bearing is configured to extend radially into the hole when the first ring on the first module enters the locked position.

17. The system of claim 15, wherein:
the first module further comprises a second ring having projections on an inner surface thereof, wherein:

opposing edges of the second ring are configured to be radially compressed from a non-compressed state to a compressed state in which the projections engage grooves on an outer surface of the first ring on the first module;

the second ring rotates freely relative to the first ring, when the second ring is in the non-compressed state; and the second ring and the first ring are rotatable as a unit from the unlocked position to the locked position, when the second ring is in the compressed state.

18. The system of claim 15, wherein the first module comprises a second ring which is axially spaced from the first ring; the first ring comprises a first set of teeth; and the second ring comprises a second set of teeth; wherein:

the first set of teeth is configured to engage the second set of teeth when the second module is pressed onto the first module;

the second ring rotates freely relative to the first ring, when the first set of teeth do not engage the second set of teeth; and the second ring and the first ring are rotatable as a unit from the unlocked position to the locked position, when the first set of teeth engage the second set of teeth.

19. A system for removably connecting an end effector to a robot arm, comprising:

an arm mount module having a front surface and a rear surface,
  wherein the arm mount module is configured to be connected to a robot arm;

an arm drape module having a front surface and a rear surface,
  wherein the rear surface of the arm drape module is configured to be removably connected to the front surface of the arm mount module by a first locking mechanism; and a third module configured to be removably connected to the arm drape module by a second locking mechanism, and to be removably connected to the end effector,
  wherein at least one of the first locking mechanism and the second locking mechanism comprises:
    a first ring mounted on a first module, the first ring being rotatable from an unlocked position to a locked position, the first ring comprising a first locking feature, wherein the first module is one of the arm mount module, the arm drape module, the hand drape module, and the hand mount module; and
    a second locking feature on a second module, the second module being removably connected to the first module, wherein the first locking feature engages the second locking feature when the first ring is in the locked position.

20. A system for removably connecting an end effector to a robot arm having a front surface and a rear surface, the system comprising:

an arm drape module having a front surface and a rear surface,
  wherein the rear surface of the arm drape module is configured to be removably connected to the robot arm by a first locking mechanism; and a hand drape module having a front surface and a rear surface,
  wherein the rear surface of the hand drape module is configured to be removably connected to the front surface of the arm drape module by a second locking mechanism; and wherein:
  the front surface of the hand drape module is configured to be removably connected to the end effector by a third locking mechanism;

wherein at least one of the first locking mechanism, the second locking mechanism, and the third locking mechanism comprises:
  a first ring mounted on a first module, the first ring being rotatable from an unlocked position to a locked position, the first ring comprising a first locking feature, wherein the first module is at least one of the arm drape module, the hand drape module, and the end effector; and
  a second locking feature on a second module, the second module being removably connected to the first module, wherein the first locking feature engages the second locking feature when the first ring is in the locked position.

21. The system of claim 20, wherein at least one of the first locking mechanism, the second locking mechanism, and the third locking mechanism comprises:

the first ring mounted on the first module, wherein the first locking feature on the first ring comprises a plurality of inwardly directed flanges having spaces therebetween; and the second locking feature on the second module, wherein the second locking feature comprises a plurality of outwardly directed flanges on the second module, wherein:
  the outwardly directed flanges on the second module are configured to be aligned with the spaces between the inwardly directed flanges on the first ring on the first module when the first ring on the first module is in the unlocked position; and
  the outwardly directed flanges on the second module are configured to be aligned with the inwardly directed flanges on the first ring on the first module when the first ring on the arm mount module is in the locked position.

22. The system of claim 1, further comprising a means for transmitting a signal and/or power to, or receiving a signal and/or electrical power from, the end effector, the means for transmitting or receiving a signal and/or electrical power comprising:

an electrical connector configured to make electrical contact with the robot arm on the rear surface of the arm mount module;

a plurality of first electrical contacts on the front surface of the arm mount module, the first electrical contacts being in electrical contact with the electrical connector;

a plurality of second electrical contacts on the arm drape module, the second electrical contacts being configured to engage the planar first electrical contacts;

a plurality of third electrical contacts on the arm drape module, the third electrical contacts being in electrical contact with the second electrical contacts;

a plurality of fourth electrical contacts on the third module, the fourth electrical contacts being configured to engage the third electrical contacts; and a plurality of fifth electrical contacts on the third module, the fifth electrical contacts being in electrical contact with the fourth electrical contacts;

wherein the electrical connector, the first electrical contacts, the second electrical contacts, the third electrical contacts, the fourth electrical contacts and the fifth electrical contacts establish a signal and power transmission pathway between the robot arm and the end effector.

23. The system of claim 1, wherein:

the system further comprises a hand mount module connected to the end effector;

the third module is a hand drape module configured to be removably connected to the arm drape module by the second locking mechanism, and to be removably connected to the hand mount module by a third locking mechanism; and the arm drape module and the hand drape module are sterile or made of sterilizable materials.

\* \* \* \* \*